United States Patent [19]
Schenker et al.

[11] 4,210,655
[45] Jul. 1, 1980

[54] ANTI-DEPRESSANT BENZOFURANYL PIPERIDINES

[75] Inventors: Karl Schenker, Binningen; Raymond Bernasconi, Oberwil, all of Switzerland

[73] Assignee: Ciba-Geigy Corporation, Ardsley, N.Y.

[21] Appl. No.: 893,104

[22] Filed: Apr. 5, 1978

Related U.S. Application Data

[63] Continuation of Ser. No. 657,652, Feb. 12, 1976, abandoned, which is a continuation-in-part of Ser. No. 446,244, Feb. 27, 1974, abandoned.

[30] Foreign Application Priority Data

Mar. 2, 1973 [CH] Switzerland ............... 3103/73

[51] Int. Cl.$^2$ ............... A61K 31/445; C07D 405/04
[52] U.S. Cl. ............... 424/267; 424/263; 542/469; 544/96; 546/196; 546/197; 546/225; 546/269; 546/270; 546/328
[58] Field of Search ............... 260/293.58, 297 B; 542/469; 424/267, 263; 546/269, 196

[56] References Cited

U.S. PATENT DOCUMENTS

| 3,470,192 | 9/1969 | Binon et al. ............... 260/297 B |
| 3,890,441 | 6/1975 | Schenker et al. ............... 424/267 |

OTHER PUBLICATIONS

Ziegler, H., et al., *Chim. Ther.*, 6, 159–166 (1971).

*Primary Examiner*—Henry R. Jiles
*Assistant Examiner*—Richard A. Schwartz
*Attorney, Agent, or Firm*—John J. Maitner

[57] ABSTRACT

Compounds of the class of (2-benzofuranyl)-1,2,3,6-tetrahydropyridines and (2-benzofuranyl)-piperidines which at the ring nitrogen atom are unsubstituted or substituted by a substituent of the class of certain aliphatic, cycloaliphatic and araliphatic radicals, and their pharmaceutically acceptable acid addition salts have valuable pharmacological properties. In particular, they inhibit monoamine oxidase and antagonize the action of tetrabenazine. They are useful as active ingredients for therapeutic compositions for the treatment of mental depression. Specific embodiments are 4-(2-benzofuranyl)-piperidine, 2-(5,6-dimethyl-2-benzofuranyl)-piperidine and their hydrochlorides.

33 Claims, No Drawings

ANTI-DEPRESSANT BENZOFURANYL PIPERIDINES

CROSS REFERENCE TO RELATED APPLICATION

This is a continuation of application Ser. No. 657,652, filed on Feb. 12, 1976, now abandoned, which is a continuation-in-part of our application Ser. No. 446 244, filed on Feb. 27, 1974 now abandoned.

DETAILED DESCRIPTION

The present invention relates to new tetrahydropyridine and piperidine derivatives having valuable pharmacological properties and therapeutic compositions containing them.

The new tetrahydropyridine and piperidine derivatives according to the invention correspond to the formula I

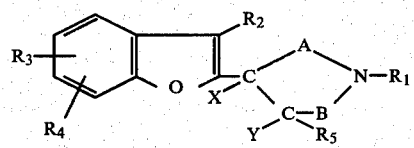

wherein $R_1$ represents hydrogen, an aliphatic hydrocarbon radical having 1–12 carbon atoms and containing at most one multiple bond, or a cycloaliphatic hydrocarbon radical having 3–12 carbon atoms and containing at most one double bond, which radicals are unsubstituted or substituted on one of their carbon atoms not bound directly to the ring nitrogen atom by hydroxy or by an oxo radical or may be interrupted by oxigen, or $R_1$ represents a phenyl-(lower alkyl)-radical in the benzene ring of which zero to three hydrogen atoms are replaced by substituents from the group consisting of halogen up to atomic number 35, lower alkyl, lower alkoxy, methylenedioxy and trifluoromethyl, and of which the lower alkyl chain is unsubstituted or substituted on one of its carbon atoms not bound directly to the ring nitrogen atom by an oxo radical or hydroxy, or it represents a cinnamyl radical unsubstituted or substituted in the benzene ring, as indicated above for the benzene ring of the phenyl-(lower alkyl)-radical, with the proviso that $R_1$ must not be methyl in the case where A represents ethylene and B represents methylene and at the same time $R_2$, $R_3$, $R_4$ and $R_5$ each represents hydrogen, $R_2$ represents hydrogen or lower alkyl, $R_3$ represents hydrogen, lower alkyl, lower alkoxy, halogen up to atomic number 35, benzyloxy, hydroxy, trifluoromethyl, 1-hydroxycycloalkyl, cycloalk-1-enyl or cycloalkyl, each of the three last-named groups having 5–8 carbon atoms, $R_4$ represents hydrogen, lower alkyl, lower alkoxy, halogen up to atomic number 35, benzyloxy or hydroxy, or $R_3$ and $R_4$ together represent trimethylene or tetramethylene or, corresponding to a fused-on benzene ring, the 1,3-butadienylene radical, $R_5$ represents hydrogen, or alkyl having at most 4 carbon atoms, and A and B each represent bivalent aliphatic hydrocarbon radicals, or one of these symbols represents the direct bond, whereby A and B together always contain 3 chain members, and together with $R_5$ have in all at most 9 carbon atoms, and X and Y each represent hydrogen, or together they represent an additional bond.

and the pharmaceutically acceptable addition salts thereof with inorganic and organic acids.

The invention likewise relates to addition salts, particularly pharmaceutically acceptable addition salts, of the compounds of the general formula I with inorganic and organic acids, as well as to the preparation of these addition salts.

In the compounds of the general formula I, $R_1$, as an aliphatic or cycloaliphatic hydrocarbon radical, optionally substituted as defined or interrupted by oxygen, is, for example: an ethyl, propyl, isopropyl, butyl, isobutyl, pentyl, isopentyl, neopentyl, hexyl, heptyl, 1-methylhexyl, octyl, nonyl, decyl, dodecyl, allyl, crotyl, 2-methylallyl, 2-propynyl, cyclopropyl, cyclopropylmethyl, cyclobutylmethyl, cyclopentyl, cyclohexyl, cycloheptyl, cyclopentylethyl, cyclohexylmethyl, 2-norbornanylmethyl, bicyclo[2.2.2]oct-2-ylmethyl, 1-adamantylmethyl, 3-cyclohexen-1-ylmethyl, 2-norbornen-5-ylmethyl, 2-hydroxyethyl, 2-hydroxypropyl, 3-hydroxypropyl, 3-hydroxybutyl, 2,3-dihydroxypropyl, acetonyl, 3-oxobutyl, 2-hydroxycyclohexyl, 2-oxocyclohexyl, 2-methoxyethyl, 2-ethoxyethyl, 2-isopropoxyethyl, 3-methoxypropyl, 2-butoxyethyl, 2,3-dimethoxypropyl, 3,3-diethoxybutyl, 2-(2-ethoxyethoxy)-ethyl, 2-cyclohexyloxyethyl, 2-(1-adamantyloxy)-ethyl, furfuryl, tetrahydrofurfuryl, (2,2-dimethyl-1,3-dioxolan-4-yl)-methyl or 2-(2-methyl-1,3-dioxolan-2-yl)-ethyl group, or, in cases not excluded under formula I, alternatively a methyl group. As a phenyl-(lower alkyl) group optionally substituted as defined, $R_1$ is preferably such a group having 1–3 carbon atoms in the lower alkyl chain. Lower alkyl and alkoxy groups as substituents of phenyl radicals contain 1–7, preferably 1–4, carbon atoms, and are primarily methyl or methoxy groups. Mentioned as examples of phenyl-(lower alkyl) radicals and cinnamyl radicals both optionally substituted as defined are: the benzyl group, the p-fluoro-, o-, m- or p-chloro-, p-bromo-, 3,4-dichloro-, p-methyl-, p-isopropyl-, o- or p-methoxy-, p-ethoxy-, p-isopropoxy-, 3,4-dimethoxy-, 3,4,5-trimethoxy-3,4-methylenedioxy- and p-trifluoromethylbenzyl groups, as well as the phenethyl, α-methylphenethyl, 2-phenylpropyl, β-hydroxyphenethyl, 3-hydroxy-3-phenylpropyl, phenacyl, 2-benzoylethyl or cinnamyl groups, which can be substituted, for example, analogously to the aforementioned benzyl groups.

$R_2$ as a lower alkyl group is especially one containing 1–4 carbon atoms, and is, in particular, the methyl group.

The substituent $R_3$ as halogen is fluorine, bromine and, in particular, chlorine; and as a lower alkyl group or lower alkoxy group it is one having 1–7, preferably 1–4, carbon atoms; for example, an ethyl, isopropyl, tert.butyl, ethoxy, propoxy, isopropoxy, butoxy or isobutoxy groups; in particular, however, it is a methyl group or methoxy group. A lower 1-hydroxyalkyl group and lower alk-1-enyl group denoted by $R_3$ preferably contain 1–5 and 2–5 carbon atoms, respectively, and are, for example, the hydroxymethyl, 1-hydroxyethyl, 1-hydroxypropyl, 1-hydroxy-1-methylethyl, 1-hydroxybutyl, 1-hydroxy-1-methylpropyl or 1-hydroxy-1-ethylbutyl group and the vinyl, prop-1-enyl, isopropenyl, but-1-enyl, 1-methylprop-1-enyl or 1-ethylprop-1-enyl group, respectively. As a 1-hydroxycycloalkyl, cycloalk-1-enyl or cycloalkyl group having 5–8 carbon atoms, $R_3$ is, for example, the 1-hydroxycycloheptyl, 1-hydroxycyclooctyl, cyclohept-1-enyl, cyclooct-1-enyl, cycloheptyl or cyclooctyl group, preferably, however, the 1-hydroxycyclopentyl, cyclopent-1-enyl or cyclopentyl group, and, in particular, the 1-hydroxycyclohexyl, cyclohex-1-enyl or cyclohexyl group.

Halogen atoms or lower alkyl or alkoxy groups $R_4$ are, for example, the radicals mentioned above as corresponding substituents $R_3$.

A trimethylene or tetramethylene group $R_3+R_4$ is preferably in the 5,6-position; while a fused-on benzene nucleus $R_3+R_4$ can be in the 5,6- or 6,7-position, especially, however, in the 4,5-position.

As a lower alkyl group, $R_5$ is, for example, an ethyl, propyl or n-butyl group, or, in particular, a methyl group.

Bivalent, saturated aliphatic hydrocarbon radicals A and B are methylene, ethylene and trimethylene radicals and corresponding lower-alkylated radicals which, together and with $R_5$, or, since one of the symbols A and B can represent the direct bond and $R_5$ hydrogn, also singly, contain at most 9 carbon atoms; such as, for example, ethylidene, propylidene, dimethylmethylene, propylene, 1-ethyl-ethylene, 1,1-dimethylethylene, 1-methyltrimethylene, 2-methyltrimethylene, 1-ethyltrimethylene, 1,1-dimethyltrimethylene or 2,2-dimethyltrimethylene radicals. In the case where A denotes the direct bond, or a radical having one or three chain-members, such as the methylene or trimethylene group, and B correspondingly a radical having three or two chain-members, or the direct bond, the symbols X and Y preferably represent hydrogen atoms; they can, however, likewise represent an additional bond.

Of particular importance is methylene as radical A together with ethylene as radical B, and above all ethylene as radical A together with methylene as radical B.

The compounds of the general formula I and their addition salts with inorganic and organic acids possess valuable pharmacological properties. After oral and subcutaneous administration in the dosis range of 2 to 100 mg/kg, they inhibit in the rat and in other species of experimental animals monoamine oxidase, in particular selectively the A-form thereof, as is shown from the results of the isotopic determination of enzyme activity. At the same time, they inhibit in the rat, with oral and subcutaneous administration of 2 to 100 mg/kg, the absorption of noradrenaline into the heart, and inhibit also the absorption of serotonin into the midbrain synaptosomes of rats. Furthermore, they inhibit, to an extent depending on the concentration, the absorption of serotonin into human blood platelets in vitro. In addition, they antagonise, in the case of intraperitoneal administration of 2 to 40 mg/kg, the action of tetrabenazine in the rat. Together with a favourable therapeutic index, the abovementioned properties characterise the compounds of the general formula I and their pharmaceutically acceptable salts with inorganic and organic acids as antidepressants which, for example, can be administered orally, rectally or parenterally for the treatment of mental depression.

Of particular importance are compounds of the general formula I in which $R_1$ represents hydrogen, and which correspond to the formula Ia

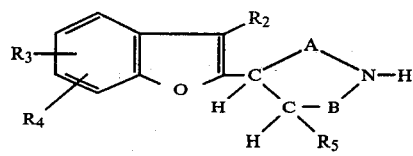

wherein
$R_2$ represents hydrogen or lower alkyl,
$R_3$ represents hydrogen, lower alkyl, lower alkoxy, halogen up to atomic number 35, benzyloxy, hydroxy, trifluoromethyl, 1-hydroxycycloalkyl, cycloalk-1-enyl or cycloalkyl, each of the three last-named groups having 5–8 carbon atoms,
$R_4$ represents hydrogen, lower alkyl, lower alkoxy, halogen up to atomic number 35, benzyloxy or hydroxy, or
$R_3$ and $R_4$ together represent trimethylene or tetramethylene or, corresponding to a fused-on benzene ring, the 1,3-butadienylene radical,
$R_5$ represents hydrogen, or alkyl having at most 4 carbon atoms, and
A and B each represent bivalent aliphatic hydrocarbon radicals, or one of these symbols represents the direct bond, whereby A and B together always contain 3 chain members, and together with $R_5$ have in all at most 9 carbon atoms,
and the pharmaceutically acceptable addition salts thereof with inorganic and organic acids.

Likewise of particular importance are compounds of the formula Ib

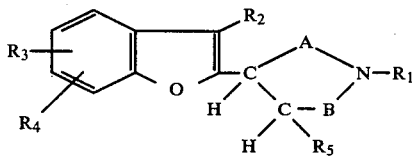

wherein $R_1$ has the meaning defined under formula I and $R_2$, $R_3$, $R_4$, $R_5$, A and B have the meanings defined under formula Ia, and the pharmaceutically acceptable acid addition salt thereof with inorganic and organic acids.

Preferred compounds of the formula Ia are those in which
$R_2$ represents hydrogen or methyl, $R_3$ represents hydrogen, halogen up to atomic number 35, lower alkyl, lower alkoxy, trifluoromethyl, 1-hydroxycycloalkyl, cycloalk-1-enyl or cycloalkyl, each of the three last named groups having 5–8 carbon atoms, $R_4$ represents hydrogen, a lower alkyl group or halogen up to atomic number 35, or $R_3$ and $R_4$ together represent trimethylene in 5,6-position or, corresponding to a fused-on benzene ring, the 1,3-butadienylene radical in 4,5-position, $R_5$ represents hydrogen or methyl and A and B represent methylene, ethylene, trimethylene or the direct bond, account being taken of the sum of chain members fixed at 3, and the pharmaceutically acceptable acid addition salts thereof.

Preferred compounds of the formula Ib are those in which $R_1$ has the meaning defined under formula I, but in particular represents alkyl having at most 4 carbon atoms, allyl, 3-oxobutyl, 3-hydroxybutyl, 2-propynyl or cyclopropylmethyl with the proviso that R₁ must not be methyl in the case where A represents ethylene and B represents methylene and at the same time R₂, R₃, R₄ and R₅ each represent hydrogen, whereas R₂, R₃, R₄, R₅, A and B have the same meanings as hereinbefore preferred for the compounds of the formula Ia, and the pharmaceutically acceptable acid addition salts thereof. Especially preferred are compounds of the formula Ia in which R₂ and R₅ represent hydrogen, R₃ represents hydrogen, halogen up to atomic number 35, methyl, methoxy or cyclohexyl, R₄ represents hydrogen, methyl, chlorine or bromine, A represents methylene and B ethylene or A represents ethylene and B methylene, and the pharmaceutically acceptable acid addition salts thereof.

Also especially preferred are compounds of the formula Ib in which R₁ has the meaning hereinbefore preferred, but is in particular 2-propynyl or cyclopropyl or in addition, if R₃ is different from hydrogen, methyl, and R₂, R₃, R₄, R₅, A and B have the meanings especially preferred for the compounds of the formula Ia, R₃ in particular representing hydrogen, chlorine, bromine, methyl or methoxy, and R₄ in particular representing hydrogen or methyl, and the pharmaceutically acceptable acid addition salts thereof. In the first line preferred are compounds of the formula Ia, in which R₂ and R₅ represent hydrogen, R₃ represents hydrogen, chlorine, bromine, methyl or methoxy, R₄ represents hydrogen or methyl, A represents methylene and B ethylene, or A represents ethylene and B methylene, and the pharmaceutically acceptable acid addition salts thereof.

Of the compounds of formula Ib those are preferred in the first line in which R₂, R₃, R₄, R₅, A and B have the meanings last-mentioned for the compounds of formula Ia, whereas R₁ represents 2-propynyl or cyclopropylmethyl. Especially important compounds are, e.g 4-(2-benzofuranyl)-piperidine, 4-(5,6-dimethyl-2-benzofuranyl)-piperidine, 3-(2-benzofuranyl)-piperidine, 1-methyl-4-(5-chloro-2-benzofuranyl)-piperidine, 4-(5-cyclohexyl-2-benzofuranyl)-piperidine, 4-(5-methoxy-7-bromo-2-benzofuranyl)-piperidine and 1-methyl-4-(5-methoxy-7-bromo-2-benzofuranyl)-piperidine, as well as their pharmaceutically acceptable acid addition salts, such as, e.g. the hydrochlorides.

The new tetrahydropyridine and piperidine derivatives of the general formula I and their acid addition salts are prepared according to the invention by a process in which, in a manner known per se, (a) in a compound of the general formula II

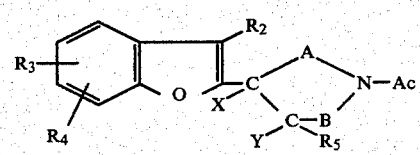
(II)

wherein
Ac represents a radical capable of being split off, and R₂, R₃, R₄ and R₅ have the meanings given under formula I, the radical Ac is split off; and, (b) optionally, a compound, obtained according to (a) or in any other manner, of the general formula Ia embraced by the general formula I

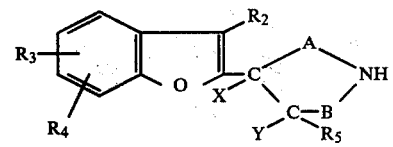
(Ia)

wherein R₂, R₃, R₄ and R₅ have the meanings given under the general formula I, is reacted with a reactive ester of a hydroxy compound of the general formula III $$HO-R_1{}^a \qquad (III)$$

wherein R₁ᵃ has the meaning given for R₁ under formula I, with the exception of hydrogen, and, in the case where in formula Ia the symbols R₂, R₃, R₄ and R₅ represent hydrogen, A the ethylene group and B the methylene group, of the methyl group, or under reducing conditions reacted with an oxo compound of the general formula IIIa $$O=R_1{}^b \qquad (IIIa)$$

wherein
R₁ᵇ represents the geminal bivalent radical corresponding to a monovalent radical R₁ᵃ;
or added to a compound of the general formula IIIb

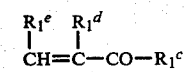
(IIIb)

wherein
R₁ᶜ, R₁ᵈ, R₁ᵉ represent separate radicals or radicals bound to each other, which supplement the group

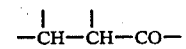

to form an oxosubstituted radical embraced by the definition of R₁;
or condensed with formaldehyde and a compound of the general formula IIIc

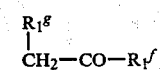
(IIIc)

wherein
R₁ᶠ and R₁ᵍ represent separate radicals or radicals bound to each other, which supplement the group

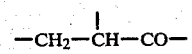

to form an oxosubstituted radical embraced by the definition of R₁; or
(c) in a compound of the general formula IV

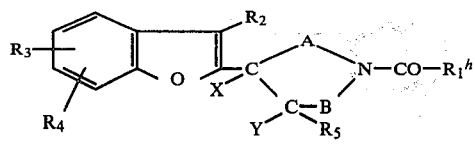 (IV)

wherein
$R_1^h$ represents a radical reduced by a methylene group, corresponding to the definition for $R_1$,
or, provided at least one of the symbols $R_2$, $R_3$, $R_4$ and $R_5$ does not represent hydrogen, and/or A does not represent the ethylene group and at the same time B not the methylene group, it can also represent a lower alkoxycarbonyl group, the carbonyl group or the alkoxycarbonyl group is reduced; or (d) a compound of the general formula V

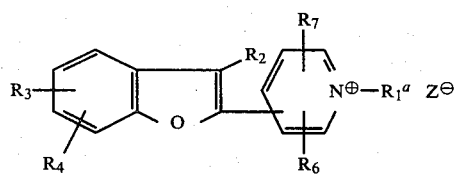 (V)

wherein
$Z^\ominus$ represents a monovalent anion or the normal equivalent of a polyvalent anion,
$R_6$ and $R_7$ represent hydrogen, or alkyl radicals having together at most 6 carbon atoms,
and $R_1^a$, $R_2$, $R_3$ and $R_4$ have the meanings given under formulae III and I,
is partially reduced to the corresponding compound of the general formula I wherein X and Y represent an additional bond; or (e) a compound of the above given general formula V, or a compound of the general formula VI

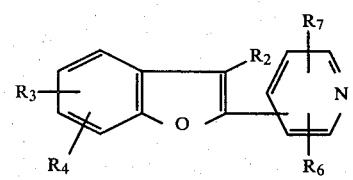 (VI)

wherein
$R_2$, $R_3$, $R_4$, $R_6$ and $R_7$ have the meanings given under formula I and formula V, or a compound of the general formula Ib embraced by the general formula I

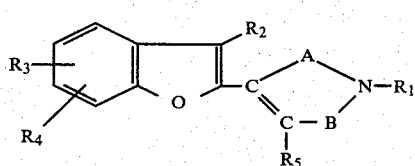 (Ib)

wherein
$R_1$, $R_2$, $R_3$, $R_4$, $R_5$, A and B have the meanings given under formula I, is catalytically hydrogenated to the corresponding piperidine compound; or (f) a compound of the general formula

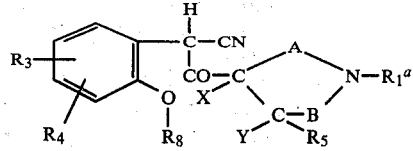 (VII)

wherein
$R_8$ represents a lower alkoxy group or lower (1-alkoxy-alkoxy)-group, the two alkoxy groups of which may also be bound to each other to form a 5- or 6-ring,
$R_1^a$ has the meaning given under formula III, and $R_3$, $R_4$, $R_5$, A, B, X and Y have the meanings given under formula I,
or an alkali metal derivative of a compound of the general formula VII, is cyclised by heating in an acid medium; or (g) a compound of the general formula I of which the group $R_1$ contains non-aromatic double or triple bonds and/or an oxo radical, and in which X and Y represent hydrogen, while $R_2$, $R_3$, $R_4$, $R_5$, A and B have the meanings given under formula I, is hydrogenated to the corresponding compound of which the group $R_1$ contains no triple bond or no, or a smaller number of, non-aromatic double bonds and/or a primary, or particularly secondary, hydroxyl group; or (h) a compound of the general formula I of which the group $R_1$ contains an oxo radical, while $R_2$, $R_3$, $R_4$, $R_5$, A, B, X and Y have the meanings given under formula I, is reduced to the corresponding compound of which the group $R_1$ contains a primary, or particularly secondary, hydroxyl group; or (i) a compound of the general formula I wherein $R_1$ represents a benzyl group optionally substituted as defined, and/or $R_3$ and/or $R_4$ represent benzyloxy groups optionally inertly substituted, and X and Y always represent hydrogen, while $R_2$, $R_5$, A and B, as well as optionally $R_4$ and/or $R_3$, have the meanings given under formula I, is subjected to hydrogenolysis; or (j) a compound of the general formula VIII

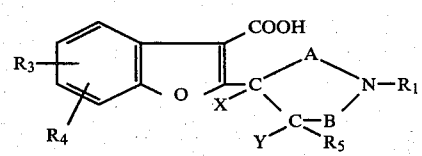 (VIII)

wherein $R_1$, $R_3$, $R_4$, X and Y have the meanings given under formula I, is heated until liberation of the approximately equimolecular amount of carbon dioxide; or (k) a compound of the general formula IX

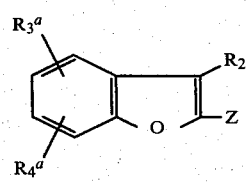 (IX)

wherein
Z represents a metal radical, $R_3{}^a$ and $R_4{}^a$ have the meanings given for $R_3$ and $R_4$ under formula I, with the exception of hydroxy groups and hydroxy-substituted radicals, and $R_2$ has the meaning given under formula I, is reacted with a reactive ester of a compound of the general formula X

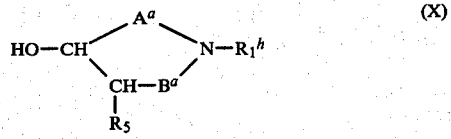

wherein
$R_1{}^h$ represents a radical corresponding to the definition given under formula I, with the exception of hydrogen and hydroxy-substituted and oxo-substituted radicals, and
$A^a$ and $B^a$ have the meanings given for A and B under formula I, with the exception of a direct bond as $A^a$ and of a radical having three chain members as $B^a$,
and $R_5$ has the meaning given under formula I; or (l) water is split off from a compound of the general formula XI

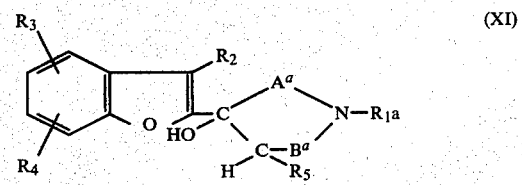

wherein
$R_2$, $R_3$, $R_4$ and $R_5$ have the meanings given under formula I, $R_1{}^a$ has the meaning given under formula III, and $A^a$ and $B^a$ have the meanings given under formula X, or from a compound of the general formula I wherein $R_3$ represents a lower 1-hydroxyalkyl group or a 1-hydroxycycloalkyl group having 5–8 carbon atoms, while $R_1$ has the meaning given under formula I, with the exception of hydrogen, and $R_2$, $R_4$, $R_5$, A, B, X and Y have the meanings given under formula I; or (m) chlorine or bromine is introduced in the 5-position into a compound of the general formula I wherein $R_1$ has the meaning given under formula I, with the exception of hydrogen as well as of oxo- and hydroxysubstituted radicals, $R_3$, $R_4$, X and Y represent hydrogen, and $R_2$, $R_5$, A and B have the meanings given under formula I, or into 1-methyl-4-(2-benzofuranyl)-piperidine; or (n) a compound of the general formula I wherein $R_1$ has the meaning given under formula I, with the exception of hydrogen and of oxo- and hydroxysubstituted radicals and halogen-substituted phenyl(lower alkyl)-radicals, $R_3$ represents chlorine or bromine, and $R_4$ hydrogen or a lower alkyl group, and $R_2$, $R_5$, A, B, X and Y have the meanings given under formula I, is converted into the corresponding compound having a metal radical at the $R_3$ position, and the last-mentioned compound reacted with a lower oxoalkane, or with a cycloalkanone having 5–8 carbon atoms; or (o) a compound of the general formula XII

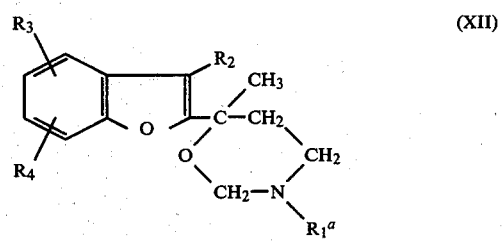

wherein $R_1{}^a$ has the meaning given under formula III, and $R_2$, $R_3$ and $R_4$ have the meanings given under formula I, or the crude reaction product from a compound of the general formula XIII

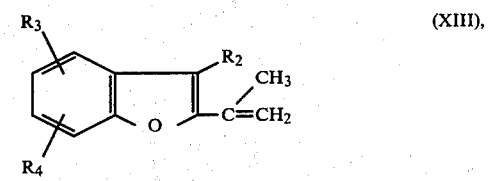

the bimolecular amount of formaldehyde and a compound of the general formula XIV

wherein $R_1$ has the meaning given under formula I, which compound is used as addition salt of a strong acid or together with such an acid, is treated with a strong acid;

and, optionally, a compound of the general formula I obtained by one of the processes defined under (a) to (o) converted into an addition salt with an inorganic or organic acid.

The radical Ac capable of being split off is, in particular, an acyl radical. The splitting-off thereof is performed, for example, by hydrolysis, solvolysis, hydrogenolysis or reduction. In the starting materials of the general formula II, Ac can be any organic acyl group, e.g. a lower alkanoyl group such as the acetyl group, an arenecarbonyl group such as the benzoyl group, an alkanesulphonyl group or arenesulphonyl group, such as the methanesulphonyl group or the p-toluenesulphonyl group, or it can also be an inorganic acyl group such as the nitroso group NO. However, acyl groups are preferred which ensure the easy obtainment of the compounds of the general formula II which contain them and/or which are relatively easily split off. Accordingly, therefore, suitable acyl groups Ac on the one hand are, in particular, acyl groups of semi-esters of carbonic acid and thiocarbonic acid, especially groups that can be split off by hydrolysis such as lower alkoxycarbonyl groups, such as the methoxycarbonyl, ethoxycarbonyl and tert.butoxycarbonyl group, also the phenoxycarbonyl group and the benzyloxycarbonyl group, as well as the methoxythiocarbonyl group and the methylthio-thiocarbonyl group; and on the other hand acyl groups of further derivatives of carbonic acid, such as the chlorocarbonyl group and, in particular, the cyano group.

The hydrolysis of compounds of the new general formula II according to process (a) can be performed in alkaline or acid medium. It is performed, for example, by prolonged heating with an alkali hydroxide, especially with sodium or potassium hydroxide, in a hydroxy compound in the presence of a little water at a temperature of between ca. 80° and 200° C. A suitable reaction medium is, for example, ethylene glycol or a lower monoalkyl ether thereof and, with performance of the hydrolysis in a closed vessel, also a lower alkanol such as methanol, ethanol or butanol. Furthermore, compounds of the general formula II, particularly those wherein Ac represents a cyano group, i.e. the acyl radical of cyanic acid, or a chlorocarbonyl group, can be hydrolysed also by being heated with a mineral acid in an organic-aqueous or aqueous medium, e.g. by several hours' boiling in a mixture of 85% phosphoric acid and formic acid, or by several hours' heating in 48% hydrobromic acid or in a mixture of hydrobromic acid and acetic acid at ca. 60°–100° C., preferably at 60°–70° C.

Further groups Ac that can be split off are the groups formed by addition of a methyl group present in place of Ac to azodicarboxylic acid di-lower-alkyl esters, which groups are split off preferably by hydrolysis in acid medium, particularly by boiling in dilute hydrochloric acid, e.g. 1 N hydrochloric acid, with liberation of hydrazodicarboxylic acid di-lower-alkyl ester and formaldehyde.

A radical that can be split off by solvolysis is, for example the tert.butoxycarbonyl radical, which can be split off under anhydrous conditions by treatment with a suitable acid, such as trifluoroacetic acid.

Acyl radicals that can be split off by reduction are, for example, α-aralkoxycarbonyl radicals, such as benzyloxycarbonyl radicals, which can be split off in the usual manner by hydrogenolysis, particularly by catalytically activated hydrogen, such as by hydrogen in the presence of a hydrogenation catalyst, for example, platinum, palladium or Raney nickel. Further radicals that can be split off by reduction are, for example, 2-haloalkoxycarbonyl radicals, such as 2,2,2-trichloroethoxycarbonyl radical or the 2-iodoethoxy- or 2,2,2-tribromoethoxycarbonyl radical, which can be split off in the usual manner, especially by metallic reduction (so-called nascent hydrogen). Nascent hydrogen can be obtained by the action of metal, or metal alloys such as amalgams, on hydrogen-releasing agents, such as carboxylic acids, alcohols or water, whereby, in particular, zinc or zinc alloys together with acetic acid are suitable. The reduction of 2-halogen-alkoxycarbonyl radicals can also be performed by means of chromium(II)-compounds, such as chromium(II)-chloride or chromium-(II)-acetate.

An acyl radical that can be split off by reduction can also be a sulphonyl group, such as a lower alkanesulphonyl group or arylsulphonyl group, such as methanesulphonyl or p-toluenesulphonyl, which can be split off in the usual manner by reduction with nascent hydrogen, e.g. by an alkali metal such as lithium or sodium, in liquid ammonia, or split off electrolytically.

The preparation of the starting materials of the general formula II will be described further on in the text.

Suitable reactive esters of compounds of the general formula III for the reaction with compounds of the general formula Ia according to process (b) are, for example, hydrohalic acid esters, especially chlorides, bromides and iodides, also lower alkanesulphonic acid esters and arenesulphonic acid esters, such as methanesulphonic acid esters, or benzenesulphonic acid esters and p-toluenesulphonic acid esters, as well as esters of other strong acids, e.g. sulphuric acid esters, such as dimethyl sulphate and diethyl sulphate. The reactions with compounds of the general formula Ia are performed preferably in the presence of an acid-binding agent in an organic solvent inert under the reaction conditions. Suitable acid-binding agents are tertiary organic bases, such as, e.g. triethylamine, pyridine, sym. collidine and, in particular, ethyldiisopropylamine, or inorganic basic substances such as, e.g. sodium carbonate or potassium carbonate; and suitable solvents, e.g. lower alkanols such as methanol, ethanol, isopropanol or butanol, ethereal compounds such as dioxane, tetrahydrofuran or 2-methoxyethanol, lower aliphatic ketones such as methyl ethyl ketone, and N-substituted acid amides such as dimethylformamide or N,N,N',N',N'',N''-hexamethylphosphoric acid triamide. The reaction temperature is between ca. 0° and 200° C., preferably between room temperature and ca. 120° C. The reaction temperatures necessary for reactions with reactive esters of primary hydroxy compounds are in most cases at the lower limit of the given ranges, while reactions with reactive esters of non-primary hydroxy compounds are mostly to be performed at higher temperatures, and accordingly in closed reaction vessels if required, whereby the use of a particularly effective acid-binding agent, such as ethyldiisopropylamine, is of advantage.

Reactions of compounds of the general formula Ia with oxo compounds of the general formula IIIa can be carried out, for example, in formic acid at a temperature of between ca. 70° and 100° C.; or optionally also by the action of hydrogen in the presence of a hydrogenation catalyst, such as, e.g. Raney nickel, platinum oxide or palladium charcoal, at normal or moderately elevated pressures and temperatures, in a suitable organic solvent, such as, e.g. ethanol or dioxane. Suitable oxo compounds are, for example, aliphatic aldehydes having at least 2 carbon atoms, aliphatic and cycloaliphatic ketones, benzaldehyde, and benzaldehyde substituted as defined. Particularly suitable, however, provided that in the compound of the general formula Ia used as reaction component at least one of the radicals $R_2$, $R_3$, $R_4$ and $R_5$ is not hydrogen, and/or A does not represent ethylene and at the same time B not methylene, is formaldehyde, which is preferably used together with formic acid as reducing agent.

The addition of compounds of the general formula Ia to unsaturated oxo compounds of the general formula IIIb is performed, for example, in an inert organic solvent, such as, e.g. benzene, at room temperature or with heating if necessary. In the starting materials of the general formula IIIb, it is preferable that at least one of the symbols $R_1{}^d$ and $R_1{}^e$ represent hydrogen; such compounds that are characterised by good reactivity and by the ease with which they can be prepared are those in which both symbols represent hydrogen.

Condensation of compounds of the general formula Ia with formaldehyde and a compound of the general formula IIIc can be performed under the usual conditions of the Mannich reaction, e.g. by the heating of the hydrochloride of a compound of the general formula Ia with formaldehyde, which is employed as an aqueous solution or as paraformaldehyde, and preferably in excess, in organic solution at a temperature of between ca. 70° and 140° C., or at the boiling temperature of the reaction medium where this is below 140° C. Suitable as solvents are, in particular, lower alkanols such as ethanol, methanol, isopropanol, butanol or isopentanol, as well as further solvents, preferably miscible with water, such as, e.g. dioxane.

Reactive esters of hydroxy compounds of the general formula III, oxo compounds of the general formula IIIa and compounds of the general formulae IIIb and IIIc are known in appreciable numbers, and others can be prepared by methods analogous to those for the known compounds. The starting materials of the general formula Ia can be prepared in general by the process given under (a). A further advantageous method of preparation for such compounds wherein X and X represent hydrogen atoms is hydrogenation, as given under (e) and additionally described later on in the text, of 2-, 3- or 4-(2-benzofuranyl)pyridines optionally substituted according to the definition for $R_2$, $R_3$, $R_4$, $R_6$ and $R_7$.

The reduction of the amide group of compounds of the general formula IV according to (c) is performed, for example, by means of lithium aluminium hydride or diborane in an ethereal solvent, such as diethyl ether, tetrahydrofuran, dibutyl ether or diethylene glycol diethyl ether, or in mixtures thereof, at a temperature of between ca. 20° and 100° C., or at the boiling temperature of the employed reaction medium, where this temperature is below 100° C. The diborane can be either prepared separately and introduced, or formed in situ from sodium borohydride and boron trifluoride etherate. The preparation of the starting materials of the general formula IV is described further on in the text.

The partial reduction of compounds of the general formula V according to (d) is preferably performed with the aid of sodium borohydride or potassium borohydride in an organic-aqueous medium, the procedure being, for example, that an aqueous solution of sodium borohydride is slowly added to the prepared solution of the starting material of the general formula V in an organic, water-miscible solvent, e.g. in a lower alkanol such as methanol or ethanol, or in mixtures thereof with water, and the reaction mixture subsequently allowed to further react for some time, with a reaction temperature of between ca. 5° and 60° C., preferably of between room temperature and 35° C., being maintained. The preparation of the starting materials of the general formula V is described further on in the text.

Catalytic hydrogenation of compounds of the general formulae V, VI and Ib can be performed with the use of normal hydrogenation catalysts; for example, with the use of noble metal catalysts, such as palladium on charcoal, or platinum oxide, rhodium catalysts such as rhodium on charcoal or on aluminium oxide, or alloy-skeleton-catalysts such as Raney nickel; in an inert organic solvent such as methanol, ethanol or dioxane, at room temperature and under normal pressure, or at moderately elevated temperatures up to ca. 100° C. and under elevated pressures up to ca. 100 bars. Hydrogenation of the tetrahydropyridine derivatives of the general formula Ib proceeds in general under conditions milder than those in the case of hydrogenation of compounds of the general formula VI, and particularly of compounds of the general formula V. Suitable for hydrogenation of the last-mentioned compounds are, in particular, rhodium/aluminium oxide catalysts. Hydrogenation reactions of compounds of the general formula Ib containing as $R_1$ an optionally substituted benzyl group, the splitting off of which is to be avoided, are advantageously performed in the presence of one equivalent of hydrogen chloride, and terminated after absorption of the equimolecular amount of hydrogen. The preparation of the starting materials of the general formula VI is described later on in the text. The starting materials of the general formula Ib are prepared, for example, by one of the aforementioned processes for the preparation of compounds of the general formula I, preferably by the partial reduction given under (d) of corresponding pyridinium salts.

For cyclisation according to (f), a compound of the general formula VII is, for example, firstly converted by being heated with an alkali metal amide or alkali metal hydride, preferably with sodium hydride, in an inert solvent, such as, e.g. dioxane, at moderately elevated temperature, preferably at ca. 80° C., into an alkali metal derivative, particularly into the sodium derivative. This can be precipitated, e.g. by addition of petroleum ether, and filtered off; and is subsequently cyclised, e.g. by being boiled in 48% hydrobromic acid, to a compound embraced by the general formula I. The preparation of starting materials of the general formula VII is described at a later stage.

Hydrogenation according to (g) can be performed essentially under the reaction conditions given for the above-mentioned process (e), and with the use of the catalysts mentioned there. Therefore, hydrogenation of a group $R_1$ suitable for the purpose can also be performed in the same operation as hydrogenation according to process (e). Mentioned as examples of groups $R_1$ that can be hydrogenated are: the allyl, 2-methylallyl, 2-propynyl, 3-cyclohexen-1-ylmethyl, 5-norbornen-2-yl, cinnamyl, 3-oxobutyl, phenacyl and 2-benzoylethyl groups.

The reduction according to (h) is performed essentially under the reaction conditions given for the above-mentioned partial reduction according to (d), preferably by means of sodium borohydride, and can also be combined with the process given under (d). Suitable reduceable groups $R_1$ are, for example, the 3-oxobutyl, phenacyl and 2-benzoylethyl groups.

The splitting off, by hydrogenolysis, of an optionally substituted benzyl group $R_1$ according to (i) is effected essentially under the reaction conditions given for the above-mentioned process (e), and with the use of the catalysts mentioned there. This hydrogenolysis reaction, therefore, can also be carried out in the same operation as hydrogenation according to (e); however, also quite feasible, as already mentioned, is in particular the selective hydrogenation of the cyclic double bond of compounds of the general formula Ib with retention of a benzyl group $R_1$. It is possible under the same reaction conditions as for process (e) to perform also the hydrogenolytic splitting off of benzyloxy groups $R_3$ and/or $R_4$ optionally inertly substituted. By inert substituents are meant those which during hydrogenolysis are not modified and which do not retard the course of the process. Such substituents are, in particular, lower alkyl groups and lower alkoxy groups, such as the methyl or methoxy groups.

Decarboxylation of compounds of the general formula VIII, the preparation of which is described further on in the text, according to process (j), is performed, for example, by heating at a temperature of ca. 250° to 300° C. and higher, preferably in the presence of an alkaline-earth metal oxide, especially calcium oxide. It is also possible, however, to convert the carboxylic acids of the general formula VIII firstly into alkali metal salts or alkaline-earth metal salts, also into copper, mercury or silver salts, and to then heat these salts at the above-mentioned temperatures.

In the starting materials of the general formula IX for process (k), the metal radical Z is a monovalent radical of a metal compound or of a metal, e.g. a halomagnesium radical, such as the Cl-Mg, Br-Mg or J-Mg radical, or the radical of an alkali metal, particularly of lithium. The reaction can be performed, in a known manner, in an inert organic solvent, especially in an ether or an ethereal solvent, such as diethyl ether or tetrahydrofuran, preferably at room temperature or at slightly elevated temperature up to the boiling temperature of the employed solvent. It is performed advantageously in an inert gas atmosphere, e.g. under nitrogen or argon. Reactive esters of compounds of the general formula X are preferably esters of strong acids, particularly of sulphonic acids, e.g. arenesulphonic acids and lower alkanesulphonic acids, such as p-toluenesulphonic acid or methanesulphonic acid, and of hydrohalic acids, especially hydrochloric or hydrobromic acid.

The splitting off of water reactions according to process (l) are performed in a known manner by heating of compounds of the general formula XI, or of compounds of the general formula I that are suitable for splitting off water, advantageously with separation of the formed water, and preferably in the presence of a strong acid, e.g. sulphuric acid, which is used concentrated but in small amounts, or of p-toluenesulphonic acid. Splitting off of water can also be performed by heating in an inert organic solvent, e.g. in a solvent not miscible with water, such as benzene, toluene or xylene, and advantageously with separation of the water.

The introduction of a chlorine or bromine atom according to process (m) can be performed in the usual manner, particularly at non-elevated temperature or with cooling, and in the presence of a catalyst such as iron, iodine, iron(III)-chloride, aluminium chloride, or the corresponding bromides.

In the compounds of the general formula I suitable as starting materials for the process according to (n), the chlorine atom or bromine atom $R_3$ is converted preferably by means of activated magnesium into a chloromagnesium or bromomagnesium radical, or replaced by means of an alkali metal compound, such as butyl lithium, by an alkali metal radical, especially the lithium radical, whereby the employed solvent is, for example, an ether or an ethereal solvent, such as diethyl ether or tetrahydrofuran. It is possible in the same medium, or optionally with the addition of an inert solvent such as benzene, to perform also the subsequent reaction with the lower oxoalkane or with the cycloalkanone as defined, for example, at temperatures of between $-10°$ C. and the boiling temperature of the reaction medium.

In the case of process (o), the strong acid used is preferably a mineral acid such as hydrochloric acid, especially concentrated hydrochloric acid, or sulphuric acid, particularly moderately diluted 66% sulphuric acid. After initial cooling for the control of the exothermic reaction, the reaction temperature is between 60° and 110° C., preferably between 90° and 100° C., the duration of reaction being between ca. 1 and 10 hours, preferably between 5 and 6 hours.

The starting materials of the general formula XII are formed, together with 1-substituted 4-(2-benzofuranyl)-4-piperidinols, which are embraced by the general formula XI, on reaction of compounds of the general formula XIII with the bimolecular amount of formaldehyde, e.g. as a 35% aqueous solution, and the equimolecular amount of a mineral acid salt, particularly the hydrochloride, of a compound of the general formula XIV, and are hence also contained in the crude reaction products usable instead of the compounds of the general formula XII. The last-mentioned are prepared under essentially the same reaction conditions as those for the subsequent process (o); however, the employed amount of a strong acid, such as conc. hydrochloric acid, is a merely equinormal amount with respect to the compound of the general formula XIV, if it is not preferred to use the compound of the general formula XIV as an acid addition salt, preferably as hydrochloride. In order to subsequently effect the rearrangement of the formed compound of the general formula XII and simultaneously the dehydration of the piperidinol also formed, it is only necessary to slowly add, with cooling, e.g. at 50°-70° C., further mineral acid, such as conc. sulphuric acid, and to complete the reaction at, e.g., 90°-95° C. According to a variant of the process, in most cases less advantageous, the formation of the crude reaction product and the rearrangement and dehydration thereof can be performed simultaneously by a process in which there is used from the start an excess of a strong acid, particularly sulphuric acid or hydrochloric acid. Compounds of the general formula XIII can be prepared, for example, by reaction of compounds of the general formula IX with acetone in a manner known per se.

The starting materials for the above-mentioned processes which are not already embraced by the general formula I and which have not already received particular mention can be prepared, in one or more stages, from compounds of the above given general formula VI. Among the last-mentioned compounds, the unsubstituted 4-(2-benzofuranyl)-pyridine, as well as 2-(2-benzofuranyl)-6-methylpyridine, and further analogues methyl-substituted in the pyridine ring or substituted in the benzene ring by chlorine or methyl, and the hydrochlorides thereof, have already been described in the Swiss Patent Specification No. 451,963 (cp. also French Patent Specification No. 5337 M, U.S. Pat. No. 3,470,192). The process of preparation given in the Swiss Patent Spec. is one in which the starting material employed is optionally substituted salicylaldehyde; this is firstly condensed by an already known process [J. Org. Chem. 21, 1039–1041 (1956)] with 4-picoline, 2-picoline or suitable dimethylpyridines in acetic anhydride to form the acetic acid ester of the optionally correspondingly substituted o-[2-(4- or 2-pyridyl)-vinyl]-phenol. From this are obtained by bromine addition the corresponding o-[1,2-dibromo-2-(4- or 2-pyridyl)-ethyl]-compounds, which are either cyclised direct by means of an alkali hydroxide or alkali alcoholate in alcoholic solution to give corresponding compounds of the general formula VI, or converted firstly with sodium acetate in acetic acid into the corresponding o-[2-bromo-2-(4- or 2-pyridyl)vinyl] compounds, which can then by cyclised fully analogously to give compounds of the general formula VI.

According to a second reaction sequence described in the Swiss Patent Specification No. 501,610, the optionally substituted salicylaldehyde is firstly converted into its methyl ether; this is reduced to the corresponding alcohol, this converted by way of the chloride into the optionally substituted (o-methoxyphenyl)-acetonitrile, this then condensed with the optionally methyl-substituted ethyl ester of isonicotinic acid or picolinic acid to the corresponding C-acylated (o-methoxyphenyl)-acetonitrile, and finally an alkali metal compound of this nitrile cyclised by the action of concentrated hydrobromic acid to the desired, optionally substituted 4- or 2-(2-benzofuranyl)-pyridine. It is possible to use in this reaction sequence also other lower alkyl esters of isonicotinic acid and picolinic acid substituted by lower alkyl groups, as well as lower alkyl esters of nicotinic acid optionally substituted by lower alkyl groups.

There has now been found a further reaction sequence leading to those starting materials of the general formula VI in which the 2-benzofuranyl radical is linked with the 4- or 2-position of the pyridine ring, which sequence in the most important cases likewise has optionally substituted salicylaldehyde as its starting material, but which is easier to perform and is shorter than the above-mentioned reaction sequences. The new process is one in which a compound of the general formula VIa

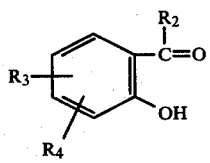

wherein $R_2$, $R_3$ and $R_4$ have the meanings given under formula I, $R_2$ however preferably represents hydrogen, is reacted, in the presence of an acid-binding agent, with a 4-(halomethyl)- or 2-(halomethyl)-pyridine, particularly with 4- or 2-(chloromethyl)-pyridine or 4- or 2-(bromomethyl)-pyridine, to give an ether of the general formula VIb

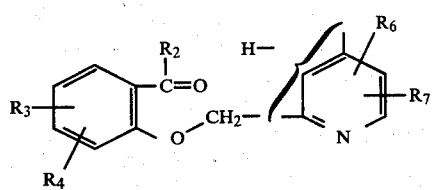

wherein $R_2$, $R_3$, $R_4$, $R_6$ and $R_7$ have the meanings given under formula I;

and this ether cyclised in the presence or absence of a condensation agent. The resulting compounds of the general formula VI are, with the exception of the compounds described in the above-mentioned Swiss patent specifications, new substances.

The reaction of compounds of the general formula VIa with 4- or 2-(chloromethyl)-pyridines or 4- or 2-(bromomethyl)-pyridines can be performed, e.g., in an inert organic solvent, such as, e.g. dimethylformamide, in the presence of an acid-binding agent, such as, e.g. sodium or potassium carbonate, at a temperature of between ca. 50° and 150° C., preferably between ca. 70° and 100° C., and, optionally, accelerated by addition of a small amount of potassium iodide or sodium iodide. The subsequent cyclisation is effected, for example, by heating of the isolated, but not necessarily purified, compounds of the general formula VIb at temperatures of between ca. 240° and 320° C. Optionally, however, cyclisation may also be performed in the same operation as that in which the formation of ether occurs, and under the reaction conditions which are in any case required for this process; or, if necessary, by heating for a longer time and/or at higher temperatures within the given range, whereby an excess of acid-binding agent may act as condensation agent.

Compounds of the general formula V are obtained from compounds of the general formula VI by quaternisation with reactive esters of hydroxy compounds of the general formula III. Quaternisation can be performed in the usual manner in an inert organic solvent, e.g. in the lower alkanol on which also the reactive ester is based, also, e.g. in ethyl acetate, tetrahydrofuran or dioxane, at room temperature or at moderately elevated temperatures up to ca. 100° C.

Starting materials of the general formula II in which the acyl radical is an acyl radical of a semiester of a carbonic acid or thiocarbonic acid, or a cyano radical or a chlorocarbonyl radical, can be prepared, for example, from corresponding compounds of the general formula I wherein $R_1$ is a group easily split off, such as the allyl or benzyl group, and particularly the methyl group, by reaction with chloroformic acid esters or chloroformic acid thioesters, especially with chloroformic acid ethyl ester, chloroformic acid tert. butyl ester, chloroformic acid benzyl ester, chloroformic acid phenyl ester or chlorothioformic acid-S-methyl ester, or with cyanogen bromide or phosgene, at elevated temperature, e.g. in toluene at the boiling temperature thereof. Instead of suitable compounds of the general formula I, it is possible to use for this reaction also 1-methyl-4-(2-benzofuranyl)-1,2,3,6-tetrahydropyridine and 1-methyl-4-(2-benzofuranyl)-piperidine. And in place of the aforementioned carbonic acid derivatives, it is also possible to use, e.g., carboxylic acid halides, such as, e.g. acetyl bromide or benzyl chloride, but the corresponding reaction for the splitting off of the group $R_1$ requires in most cases more energetic conditions, and is less complete than the reaction occurring, e.g. with the use of chloroformic acid ethyl ester and, in particular, cyanogen bromide. The reaction sequence consisting of the reaction of suitable compounds of the general formula I with chloroformic acid esters, cyanogen bromide, or similar reagents, and the subsequent hydrolysis according to (a) is of importance for, in particular, the preparation of final materials of the general formula I wherein $R_1$ represents a hydrogen atom, and X and Y together represent an additional bond. Hence, the compounds started with in the preparation of such starting materials of the general formula II are, in particular, compounds of the more restricted general formula Ib in which $R_1$ is a methyl, allyl or benzyl group. Likewise starting with compounds of the general formula Ib wherein $R_1$ is a methyl group, there are obtained, by reaction with azodicarboxylic acid di-loweralkyl esters, such as azodicarboxylic acid diethyl ester, e.g. in methanol, or preferably by several hours' boiling in cyclohexane, the corresponding adducts; cp. in this connection Liebigs Ann. Chem. 590, 37–54 (1954) and J.prakt.Chem (4) 26, 218–224 (1964). Of the starting materials of the general formula II having a group —NO as acyl radical Ac, the ones of particular interest are those which carry on the carbon atom adjacent to the acylated nitrogen atom a methyl group or other lower alkyl group, which has been introduced into relevant compounds without this group by metallisation and subsequent reaction with a lower alkyl halide.

Starting materials of the general formula IV for the reduction according to (c), particularly those having an additional bond in the position of X and Y, can be prepared by a process identical or analogous to that for the aforementioned preparation of starting materials of the general formula II, the process comprising the reaction of suitable carboxylic acid halides with corresponding compounds of the general formula I, especially compounds of the more restricted formula Ib having a methyl group as $R_1$, or with 1-methyl-4-(2-benzofuranyl)-1,2,3,6-tetrahydropyridine. It is, however, more advantageous, especially for the preparation of compounds of the general formula IV having hydrogen atoms as X and Y, to start with compounds of the general formula Ia, particularly with the compounds of this formula having hydrogen atoms as X and Y and being easily obtainable by hydrogenation according to process (e); and to acylate the imino group thereof in the usual manner, e.g. by reaction with suitable carboxylic acid halides, i.e. with those corresponding to the definition of $R_1^h$, in the presence of acid binding agents, such as, e.g. potassium carbonate, in an inert organic solvent, such as, e.g. dioxane, or in pyridine or in mixtures thereof with inert organic solvents, at room temperature or at moderately elevated temperatures.

Starting materials of the general formula VII can be prepared by a reaction sequence analogous, for example, to that previously mentioned and described in the Swiss Patent Specification No. 501 610, for which there is used an ethyl ester of 1,2,3,6-tetrahydroisonicotinic acid or of isonipecotic acid each substituted in the 1-position according to the definition for $R_1^a$ and optionally in the ring by lower alkyl groups, or corresponding hydrogenated derivatives of the nicotinic acid series or picolinic acid series.

Among the starting materials of the general formula VIII, the ones that can be prepared in a simple manner are, in particular, those in which $R_3$ is a 5-hydroxy group, the procedure being such that, by a reaction sequence analogous to one published by A. N. Grinev et al., e.g. in J.Gen.Chem. USSR 27, English translation p.897 (1957), p-benzoquinone is condensed with isonicotinoylacetic acid ethyl ester to 2-(4-pyridyl)-5-hydroxy-3-benzofurancarboxylic acid ethyl ester, this converted, e.g. by a process analogous to the processes given under (b), (d) and (e), into a 2-(1,2,3,6-tetrahydro-4-pyridyl)- or 2-(4-piperidyl)-5-hydroxy-3-benzofurancarboxylic acid ethyl ester both substituted on the nitrogen atom according to the definition for $R_1$, and this product then hydrolysed to the free carboxylic acid.

Compounds of the general formula IX are obtained, for example, from appropriate compounds, halogen-substituted in the 2-position, with magnesium, or particularly from appropriate compounds unsubstituted in the 2-position, of which various ones are known, with alkali metal compounds, such as butyl lithium, in situ, i.e. in the medium serving also for the subsequent reaction with reactive esters of compounds of the general formula X. Of the last-mentioned starting materials, some are known, and others can be prepared analogously to these from corresponding known compounds of the general formula X.

Starting materials of the general formula XI are obtained, in particular, by reaction of compounds of the previously given general formula IX with 4-piperidones and 3-piperidones, each substituted according to the definition for $R_1^a$ and, optionally, according to the definitions for $R_5$, $A^a$ and $B^a$, of which some are known and others can be prepared in a manner analogous to that for the known compounds.

The present invention relates also to such modifications of the processes given under (a) to (o) and to preliminary stages thereof, whereby a process is interrupted at some stage, or whereby a compound occurring as intermediate at some stage is used as starting material and the uncompleted steps performed, or whereby a starting material is formed under the reaction conditions, or, optionally, is used in the form of a salt. If the required starting substances are optically active, then both the racemates and the isolated antipodes can be used, or in the case of diastereomeric compounds either mixtures of racemates or specific racemates, or likewise isolated antipodes. Also such starting substances can, optionally, be used in the form of salts. The starting materials preferably used for the carrying out of the reactions according to the invention are those from which are obtained the groups of final materials to which particular reference was made at the commencement of the text.

Depending on the conditions of the process and on the starting materials, the starting materials are obtained in the free form, or in the form, likewise included in the invention, of their acid addition salts, or, optionally, also as hydrates of the last-mentioned. The acid addition salts of the new compounds of the general formula I can be converted in a known manner into the free bases; e.g., with basic agents, such as alkalies or ion exchangers. On the other hand, the compounds of the general formula I obtained by the process according to the invention can, optionally, be converted in the usual manner into their addition salts with inorganic or organic acids. For example, the acid desired as salt component is added to a solution of a compound of the general formula I in an organic solvent. Solvents preferably used for the reaction are those in which the occurring salt is difficultly soluble, so that the salt can be separated by filtration. Such solvents are, for example, ethyl acetate, methanol, ether, acetone, methyl ethyl ketone, acetone/ether, acetone/ethanol, methanol/ether and ethanol/ether.

It is possible to use as pharmaceutic active substances, instead of free bases, pharmaceutically acceptable acid addition salts, i.e. salts with acids of which the anions are not toxic in the dosage amounts concerned. Moreover, it is of advantage if the salts to be used as pharmaceutic active substances readily crystallise, and are not, or only slightly, hygroscopic. For salt formation with compounds of the general formula I, it is possible to use, e.g. hydrochloric acid, hydrobromic acid, sulphuric acid, phosphoric acid, methanesulphonic acid, ethanesulphonic acid, 2-hydroxyethanesulphonic acid, acetic acid, lactic acid, succinic acid, fumaric acid, maleic acid, malic acid, tartaric acid, citric acid, benzoic acid, salicylic acid, phenylacetic acid, mandelic acid and embonic acid.

The new compounds can be present, depending on the choice of starting materials and working procedures, as optical antipodes or racemates or, if they have at least two asymmetric carbon atoms, also as mixtures of isomers (racemate mixtures). The mixtures of isomers (racemate mixtures) obtained can, by virtue of the physical-chemical differences in the constituents, be separated in a known manner into the two stereoisomeric (diastereomeric) pure racemates, e.g. by chromatography and/or fractional crystallisation.

Resulting racemates can be resolved by known methods, for example, by recrystallisation from an optically active solvent, with the aid of microorganisms, or by reaction with an optically active acid forming salts with the racemic compound, and separation of the salts obtained in this manner, e.g. by virtue of their different degrees of solubility, into the diastereomers from which the antipodes can be liberated by the action of suitable agents. Particularly suitable optically active acids are, for example, the D- and L-forms of tartaric acid, di-o-toluyltartaric acid, malic acid, mandelic acid, camphorsulphonic acid or quinic acid. It is of advantage to isolate the more effective of the two antipodes.

The new compounds are administered orally, rectally or parenterally. The dosage amount depends on the mode of administration, on the species, on the age and on the individual condition. The daily doses of the free bases, of their 5-oxides or of pharmaceutically acceptable salts of the free bases vary between 0.1 mg/kg and 10 mg/kg for warm-blooded animals. Suitable dosage units, such as dragées, tablets, suppositories or ampoules, preferably contain 5–100 mg of an active substance according to the invention.

Dosage units for oral administration contain as active substance preferably between 5 and 90% of a compound of the general formula I, or of a pharmaceutically acceptable salt thereof. The said dosage units are produced by combination of the active substance with, e.g. solid pulverulent carriers, such as lactose, saccharose, sorbitol or mannitol; starches such as potato starch, maize starch or amylopectin, also laminaria powder or citrus pulp powder; cellulose derivatives or gelatine, optionally with the addition of lubricants, such as magnesium or calcium stearate or polyethylene glycols, to form tablets or dragée cores. The dragée cores are coated, for example, with concentrated sugar solutions which can also contain, e.g. gum arabic, talcum and/or titanium dioxide, or with a lacquer dissolved in readily volatile organic solvents or solvent mixtures. Dyestuffs can be added to these coatings, e.g. for identification of the various dosage amounts.

Further suitable oral dosage units are hard gelatine capsules, as well as soft closed capsules made from gelatine and a softener such as glycerin. The hard gelatine capsules contain the active substance preferably as a granulate, e.g. in admixture with fillers such as maize starch, and/or lubricants such as talcum or magnesium stearate, and optionally stabilisers such as sodium metabisulphite ($Na_2S_2O_5$) or ascorbic acid. In soft capsules, the active substance is preferably dissolved or suspended in suitable liquids, such as in polyethylene glycols, whereby likewise stabilisers may be added.

Suitable dosage units for rectal administration are, e.g. suppositories consisting of a combination of an active substance with a suppository foundation substance. Applicable suppository foundation substances are, e.g. natural or synthetic triglycerides, paraffin hydrocarbons, polyethylene glycols or higher alkanols. Also suitable are gelatine rectal capsules consisting of a combination of the active substance with a foundation substance. Suitable foundation substances are, e.g. liquid triglycerides, polyethylene glycols or paraffin hydrocarbons.

Ampoules for parenteral administration, especially intramuscular administration, preferably contain a water-soluble salt of an active substance in a concentration preferably of 0.5–5%, optionally together with suitable stabilisers and buffer substances, in aqueous solution.

The following examples further illustrate the preparation of tablets, dragees, capsules, suppositories and ampoules:

(a) 250 g of 4-(2-benzofuranyl)-piperidine-hydrochloride is mixed with 175.80 g of lactose and 169.70 g of potato starch; the mixture is moistened with an alcoholic solution of 10 g of stearic acid, and then granulated through a sieve. After drying of the granulate, 160 g of potato starch, 200 g of talcum, 2.50 g of magnesium stearate and 32 g of colloidal silicon dioxide are mixed in, and the mixture is subsequently pressed out to form 10,000 tablets each weighing 100 mg and each containing 25 mg of active substance; optionally, the tablets can be provided with grooves to effect a more precise adjustment of the dosage amount.

(b) A granulate is prepared from 250 g of 4-(5,6-dimethyl-2-benzofuranyl)-piperidine-hydrochloride, 175.90 g of lactose and the alcoholic solution of stearic acid; after drying, the granulate is mixed with 56.60 g of colloidal silicon dioxide, 165 g of talcum, 20 g of potato starch and 2.50 g of magnesium stearate; the mixture is subsequently pressed out to form 10,000 dragée cores. These are afterwards coated with a concentrated syrup prepared from 502.28 g of cryst. saccharose, 6 g of shellac, 10 g of gum arabic, 0.22 g of dyestuff and 1.5 g of titanium dioxide, and finally dried. The dragées obtained each weigh 120 mg and each contain 25 mg of active substance.

(c) To prepare 1000 capsules each containing 10 mg of active substance, 10 g of 4-(5-methoxy-2-benzofuranyl)-piperidine-hydrochloride are mixed with 248 g of lactose; the mixture is uniformly moistened with an aqueous solution of 2 g of gelatine, and then granulated through a suitable sieve (e.g. sieve III according to Ph.Helv. V). The granulate is mixed with 10.0 g of dried maize starch and 15.0 g of talcum, and the mixture evenly filled into 1000 hard gelatine capsules, size 1.

(d) A suppository mixture is prepared from 2.5 g of 1-methyl-4-(5-chloro-2-benzofuranyl)-piperidine-hydrochloride and 167.5 g of adeps solidus, and the mixture used to pour 100 suppositories each containing 25 mg of active substance.

(e) A solution of 10.0 g of 3-(2-benzofuranyl)-piperidine-hydrochloride in one liter of water is filled into 1000 ampoules, and then sterilised. An ampoule contains a 1% solution of 10 mg of active substance.

The following examples further illustrate the preparation of the new compounds of the general formula I and of intermediates not hitherto described; these examples, however, are in no way intended to limit the scope of the invention. Temperatures are expressed in degrees Centigrade.

EXAMPLE 1

81.0 g of 4-(2-benzofuranyl)-pyridine is dissolved in 1.5 liters of ethanol, and the solution hydrogenated in the presence of 10.0 g of palladium charcoal (5%) at a temperature of between 70° and 80° and with an initial pressure of 80 bars. After 15 hours, 25.8 liters of hydrogen has been absorbed. Hydrogenation is then terminated, the catalyst filtered off, and the filtrate concentrated in vacuo. The residue is fractionally distilled in high vacuum: the fraction distilling at 122° to 129° and 0.10 Torr is 4-(2-benzofuranyl)-piperidine. The hydrochloride prepared from this with a solution of hydrogen chloride in ethyl acetate melts, after recrystallisation from acetone, at 228°–230°.

The 4-(2-benzofuranyl)-pyridine used as starting material can be prepared in the following manner:

(a) 146.4 g of salicylaldehyde, 196.8 g of 4-(chloromethyl)-pyridine hydrochloride, 750 g of potassium carbonate and 2 g of potassium iodide are heated in 3 liters of dimethylformamide, with stirring, for 15 hours at 80°–90°. The solution is then filtered under suction, and the filter residue subsequently washed with 1 liter of chloroform. The combined filtrates are concentrated in vacuo, and the residue dissolved in 1 liter of chloroform. The organic phase is washed first with 1 liter of 2 N sodium hydroxide and then with 1 liter of water; it is subsequently dried over sodium sulphate, filtered under suction, and concentrated by evaporation. The crude o-[(4-pyridyl)-methoxy]-benzaldehyde remaining behind is further processed without purification.

(b) 290 g of o-[(4-pyridyl)-methoxy]-benzaldehyde is heated for 30 minutes at 300° under nitrogen. After cooling, the residue is dissolved in a little methylene chloride, and the solution chromatographed through 3 kg of aluminium oxide (activity II, neutral). The first fraction, eluted with 4 liters of methylene chloride, is 4-(2-benzofuranyl)-pyridine. After recrystallisation from ethanol, the compound melts at 132°-133°.

EXAMPLE 2

11 g of 4-(5-methoxy-2-benzofuranyl)-pyridine is dissolved in 240 ml of methanol, and the solution then hydrogenated in the presence of 5 g of rhodium charcoal catalyst (5%) at a temperature of between 40° and 50° and with an initial pressure of 4 bars. After 90 hours, 3.3 liters of hydrogen has been absorbed. Hydrogenation is terminated, the catalyst filtered off, and the filtrate concentrated in vacuo. The residue is fractionally distilled in high vacuum. The fraction distilling at 120° to 128° and 0.10 Torr is 4-(5-methoxy-2-benzofuranyl)-piperidine. The hydrochloride prepared from this with a solution of hydrogen chloride in ethyl acetate melts, after recrystallisation from acetone, at 220°-222°.

The 4-(5-methoxy-2-benzofuranyl)-pyridine used as starting material can be prepared in the following manner:

(a) 65.6 g of 5-methoxysalicylaldehyde, 74 g of 4-(chloromethyl)-pyridine-hydrochloride, 280 g of potassium carbonate and 2 g of potassium iodide are heated in 800 ml of dimethylformamide for 20 hours at 100°. The solution is thereupon filtered off under suction, and the filter residue subsequently washed with 1 liter of chloroform. The combined filtrates are concentrated in vacuo, and the residue is dissolved in 1 liter of chloroform. The organic phase is washed first with 500 ml of 2 N sodium hydroxide solution and then with 1 liter of water; it is afterwards dried over sodium sulphate, filtered, and concentrated by evaporation. The 4-(5-methoxy-2-benzofuranyl)-pyridine remaining behind melts, after recrystallisation from ethyl acetate, at 123°. The hydrochloride, prepared with a solution of hydrogen chloride is ethyl acetate, is recrystallised from ethyl acetate and melts then at 228°.

EXAMPLE 3

11 g of 4-(7-methoxy-2-benzofuranyl)-pyridine is hydrogenated fully analogously to Example 2, whereby 4-(7-methoxy-2-benzofuranyl)-piperidine is obtained, which is converted analogously to Example 2 into its hydrochloride, M.P. 174°.

Likewise analogously to Example 2, there is obtained, by hydrogenation of 12.5 g of 4-(5,6-dimethoxy-2-benzofuranyl)-pyridine, 4-(5,6-dimethoxy-2-benzofuranyl)-piperidine, M.P. 95-98, and its hydrochloride, M.P. 227°-229°.

The 4-(7-methoxy-2-benzofuranyl)-pyridine used as starting material can be prepared in the following manner:

(a) 106.5 g of ortho-vanillin, 116 g of 4-(chloromethyl)-pyridine-hydrochloride, 420 g of sodium carbonate and 2 g of sodium iodide are heated in 1000 ml of dimethylformamide for 15 hours at 90°-95°. The mixture is then filtered, and the filter residue washed with 1 liter of chloroform. The combined filtrates are concentrated in vacuo, and the residue is dissolved in 1 liter of chloroform. The organic phase is washed first with 500 ml of 2 N sodium hydroxide solution and then with 1 liter of water; it is subsequently dried over sodium sulphate, filtered, and concentrated by evaporation. The residue after concentration is a mixture of 4-(7-methoxy-2-benzofuranyl)-pyridine and 2-[(4-pyridyl)-methoxy]-3-methoxybenzaldehyde, and is further processed without purification.

(b) 140 g of the mixture obtained according to (a) is heated under nitrogen for 4 minutes at 250°. After cooling, the residue is dissolved in a little methylene chloride, and chromatographed through 2000 g of aluminium oxide (activity II, neutral). The first fraction, eluted with 4 liters of methylene chloride, is 4-(7-methoxy-2-benzofuranyl)-pyridine. After recrystallisation from ether, the compound melts at 138°-141°. The hydrochloride, prepared with a solution of hydrogen chloride in ethyl acetate, melts at 240°-242°.

Analogously to (a), there is obtained, starting with 127.5 g of 4,5-dimethoxysalicylaldehyde, a crude mixture of 2-[(4-pyridyl)-methoxy]-4,5-dimethoxybenzaldehyde and the cyclisation product thereof.

This mixture is converted, analogously to (b), completely into 4-(5,6-dimethoxy-2-benzofuranyl)-pyridine, M.P. 129°-133°; hydrochloride M.P. 241°-242°.

EXAMPLE 4

20 g of 4-(5-methyl-2-benzofuranyl)-pyridine is dissolved in 350 ml of ethanol, and the solution hydrogenated in the presence of one equivalent of hydrogen chloride and 4 g of palladium charcoal (5%) at a temperature of between 70° and 80° and with an initial pressure of 80 bars. The theoretical amount of hydrogen is absorbed after 15 hours. Hydrogenation is terminated, the catalyst filtered off, and the filtrate concentrated in vacuo. The residue is dissolved in 500 ml of 10% aqueous methanesulphonic acid solution and the acid solution extracted with ether. The aqueous solution is then adjusted by addition of 30% sodium hydroxide solution to have a pH value of 12, and extracted with 1 liter of chloroform. The chloroform solution is dried with sodium sulphate, filtered, and concentrated by evaporation. The residue is fractionally distilled in high vacuum. The filtrate distilling at 120°-125° and 0.1 Torr is 4-(5-methyl-2-benzofuranyl)-piperidine, which, after recrystallisation from pentane, melts at 51°-53°. The hydrochloride, prepared therefrom with a solution of hydrogen chloride in ethyl acetate, melts at 158°-161°.

The 4-(5-methyl-2-benzofuranyl)-pyridine used as starting material can be prepared in the following manner:

(a) 173.8 g of 5-methylsalicylaldehyde, 210 g of 4-(chloromethyl)-pyridine-hydrochloride, 620 g of potassium carbonate and 7 g of potassium iodide are heated in 1000 ml of dimethylformamide, with stirring, for 20 hours at 80°-90°. The solution is thereupon filtered off under suction, the filter residue concentrated with 500 ml of dimethylformamide in vacuo, and the resulting residue dissolved in 1 liter of chloroform. The organic phase is washed first with 1 liter of 1 N sodium hydroxide solution and then with 1 liter of water; it is subsequently dried over sodium sulphate, filtered off under suction, and concentrated by evaporation. The oil remaining is a mixture of 2-[(4-pyridyl)-methoxy]-5-methyl-benzaldehyde and 4-(5-methyl-2-benzofuranyl)-pyridine, and is distilled in high vacuum. The fraction distilling at 170°–190° and 0.1 Torr is dissolved for further purification in a little methylene chloride, and the solution chromatographed through 3 kg of aluminium oxide (activity II, neutral). The first fraction, eluted with 4 liters of methylene chloride, is 4-(5-methyl-2-benzofuranyl)-pyridine. The compound after recrystallisation from pentane melts at 160°–162°.

EXAMPLE 5

10.0 g of 4-(2-benzofuranyl)-piperidine (see Example 1) and 6.0 g of 3-bromopropine are dissolved in 200 ml of methanol; and the solution, after the addition of 50 g of potassium carbonate, is then stirred for 30 hours at room temperature. The reaction mixture is afterwards filtered with suction, and the filter residue washed with 500 ml of chloroform; the combined filtrates are subsequently concentrated in vacuo. The residue is dissolved in a little methylene chloride, and the solution chromatography through 300 g of aluminium oxide (activity II, neutral). The first fractions, eluted with in all 1 liter of methylene chloride, contain 1-(2-propynyl)-4-(2-benzofuranyl)-piperidine. The base is recrystallised from hexane, and thereupon melts at 75°–77°. The hydrochloride prepared with a solution of hydrogen chloride in ethyl acetate is recrystallised from ethyl acetate, and then melts at 203°–205°.

In an analogous manner there are obtained, starting with 11.4 g of 4-(5,6-dimethyl-2-benzofuranyl)-piperidine (see Example 31): 1-(2-propynyl)-4-(5,6-dimethyl-2-benzofuranyl)-piperidine, M.P. 104°–106°, and the hydrochloride thereof, M.P. 231°–233°.

EXAMPLE 6

5.8 g of 4-(2-benzofuranyl)-piperidine (see Example 1), 27 ml of N,N-di-isopropyl-ethylamine and 27 g of isopropyl bromide are refluxed in 100 ml of isopropanol for 15 hours. The solution is afterwards concentrated in vacuo and the residue dissolved in 500 ml chloroform; the organic phase is washed first with 500 ml of 1 N sodium hydroxide solution and then with 500 ml of water; it is dried over sodium sulphate, filtered, and concentrated by evaporation. The 1-isopropyl-4-(2-benzofuranyl)-piperidine-hydrochloride prepared from the resulting crude base with a solution of hydrogen chloride in ethyl acetate melts, after recrystallisation from ethyl acetate, at 186°–188°.

EXAMPLE 7

10.0 g of 4-(2-benzofuranyl)-piperidine (see Example 1) and 6.0 g of allyl bromide are dissolved in 250 ml of methanol, and the solution, after the addition of 50 g of sodium carbonate, stirred for 48 hours at room temperature. The reaction mixture is then filtered with suction, and the filter residue washed with 500 ml of chloroform. The combined filtrates are washed with 300 ml of 2 N sodium hydroxide solution, dried, and concentrated by evaporation. The residue is dissolved in a little methylene chloride, and the solution chromatographed through 500 g of aluminium oxide (activity II, neutral). The first fractions, eluted with in all 2 liters of methylene chloride, contain 1-allyl-4-(2-benzofuranyl)-piperidine. The hydrochloride prepared with a solution of hydrogen chloride in ethyl acetate is recrystallised from ethyl acetate, and then melts at 224°.

EXAMPLE 8

A solution of 6.0 g of 4-(2-benzofuranyl)-piperidine (see Example 1) and 6.0 g of methyl vinyl ketone in 100 ml of benzene is stirred for 24 hours at room temperature. The solvent is then evaporated off in vacuo (bath temperature maximum 45°). A solution of hydrogen chloride in ethyl acetate is added to the evaporation residue, and the resulting 1-(3-oxo-butyl)-4-(2-benzofuranyl)-piperidine-hydrochloride ([2-[4-(2-benzofuranyl)-piperidino]-ethyl]-methyl-ketone-hydrochloride) filtered off. It melts at 184°–186°.

EXAMPLE 9

A solution of 14.5 g of 1-(cyclopropylcarbonyl)-4-(2-benzofuranyl)-piperidine in 100 ml of tetrahydrofuran is added dropwise to a refluxing solution of 13.5 g of lithium aluminium hydride in 200 ml of tetrahydrofuran. After 15 hours' refluxing, the reaction mixture is cooled, and the excess lithium aluminium hydride broken down at −10° by means of 15 ml of water, 15 ml of 10% sodium hydroxide solution and 45 ml of water. The reaction solution is filtered off under suction and the filter residue subsequently washed with 1 liter of chloroform; the combined filtrates are then concentrated in vacuo. The residue is dissolved in 500 ml of 2 N hydrochloric acid, and the acid solution washed with ether. The aqueous solution is thereupon adjusted by addition of 10% sodium hydroxide solution to pH 12, and extracted with 1 liter of chloroform. The chloroform solution is dried with sodium sulphate, filtered off with suction, and concentrated by evaporation to obtain crude 1-(cyclopropylmethyl)-4-(2-benzofuranyl)-piperidine. After recrystallisation from hexane, the free base melts at 68°. The hydrochloride is prepared with hydrogen chloride in ethyl acetate, and recrystallised from ethyl acetate, whereupon it melts at 223°–225°.

In an analogous manner there are obtained, by reduction of 16.0 g of 1-(cyclopropylcarbonyl)-4-(5,6-dimethyl-2-benzofuranyl)-piperidine: 1-(cyclopropylmethyl)-4-(5,6-dimethyl-2-benzofuranyl)-piperidine, M.P. 80°–83°, and the hydrochloride thereof, M.P. 184°–186°.

The 1-(cyclopropylcarbonyl)-4-(2-benzofuranyl)-piperidine used as starting material can be prepared in the following manner:

12.1 g of 4-(2-benzofuranyl)-piperidine is dissolved in 250 ml of dioxane, and to the solution there are then added 7.35 g of cyclopropanecarbonyl chloride and 50 g of potassium carbonate. The reaction solution is stirred for 15 hours at room temperature. The reaction solution is thereupon filtered with suction, and the filter residue subsequently washed with 1 liter of chloroform; the combined filtrates are afterwards concentrated in vacuo. The residue is dissolved in 250 ml of ethyl acetate, and the solution successively washed with 2 N hydrochloric acid, water, 2 N ammonium hydroxide, and water; it is dried over sodium sulphate, filtered and concentrated by evaporation. The oily evaporation residue is, according to chromatographical analysis, homgeneous 1-(cyclopropylcarbonyl)-4-(2-benzofuranyl)-piperidine, which can be used for reduction with lithium aluminium hydride.

In an analogous manner is obtained, starting with 13.7 g of 4-(5,6-dimethyl-2-benzofuranyl)-piperidine (see Example 31): 1-(cyclopropylcarbonyl)-4-(5,6-dimethyl-2-benzofuranyl)-piperidine.

EXAMPLE 10

A solution of 27.6 g of 1-(3,4,5-trimethoxybenzoyl)-4-(2-benzofuranyl)-piperidine in 150 ml of tetrahydrofuran is added dropwise to a refluxing solution of 4.0 g of lithium aluminium hydride in 120 ml of tetrahydrofuran. After 4 hours' refluxing, the reaction mixture is cooled, and the excess lithium aluminium hydride decomposed at −10° by means of 4 ml of water. The reaction solution is filtered off under suction, the filter residue then washed with 1 liter of chloroform, and the combined filtrates concentrated in vacuo. The residue is dissolved in 500 ml of 10% aqueous methanesulphonic acid, and the acid solution washed with ether. The aqueous phase is thereupon adjusted to pH 12 by addition of 30% sodium hydroxide solution, and extracted with 1 liter of chloroform. The chloroform solution is dried with sodium sulphate, filtered, and concentrated by evaporation to obtain crude 1-(3,4,5-trimethoxybenzyl)-2-(2-benzofuranyl)-piperidine. The hydrochloride is prepared with hydrogen chloride in ethyl acetate, and recrystallised from ethyl acetate, whereupon it melts at 212°.

The 1-(3,4,5-trimethoxybenzoyl)-4-(2-benzofuranyl)-piperidine used as starting material can be prepared in the following manner:

(a) A solution of 18.4 g of 3,4,5-trimethoxybenzoyl chloride is added dropwise, with stirring and external cooling, to a solution of 72.0 g of 4-(2-benzofuranyl)-piperidine (see Example 1) and 50 g of sodium carbonate in 100 ml of dioxane, the manner of addition being such that the reaction temperature does not exceed 50°. The reaction solution is subsequently stirred for 15 hours at room temperature. The reaction solution is then filtered under suction, the filter residue washed with 500 ml of chloroform, and the combined filtrates concentrated in vacuo. The residue is dissolved in 250 ml of ethyl acetate, and the solution successively washed with 2 N hydrochloric acid, water, 2 N aqueous ammonia solution, and water; it is subsequently dried over sodium sulphate, filtered, and concentrated by evaporation. The resulting 1-(3,4,5-trimethoxybenzoyl)-4-(2-benzofuranyl)-piperidine melts, after recrystallisation from hexane, at 131°-134°.

EXAMPLE 11

Analogously to Example 10, 8.0 g of 1-acetyl-4-(2-benzofuranyl)-piperidine in 100 ml of tetrahydrofuran is reduced with 12.0 g of lithium aluminium hydride in 150 ml of tetrahydrofuran, whereby the reaction mixture is refluxed for 15 hours. The crude 1-ethyl-4-(2-benzofuranyl)-piperidine obtained is converted into the hydrochloride which, after recrystallisation from ethyl acetate, melts at 198°.

The starting material is prepared as follows:

(a) 150 ml of acetic anhydride is added to a solution of 7.0 g of 4-(2-benzofuranyl)-piperidine (see Example 1) in 100 ml of pyridine, and the whole stirred first for 15 hours at room temperature and then for 2 hours at 45°. The reaction mixture is thereupon concentrated in vacuo, the residue dissolved in ethyl acetate, and this solution successively washed twice with 2 N hydrochloric acid, 2 N aqueous ammonia solution, and water; it is subsequently dried over sodium sulphate and concentrated by evaporation. The crude 1-acetyl-4-(2-benzofuranyl)-piperidine remaining behind can be further processed direct. A sample of the substance recrystallised from pentane melts at 95°-97°.

EXAMPLE 12

A solution of 70 g of sodium borohydride in 150 ml of water is added dropwise, with stirring and external cooling, to a solution of 70 g of 1-methyl-4-(5-chloro-2-benzofuranyl)-pyridinium-iodide in 500 ml of methanol, the manner of addition being such that the reaction temperature does not exceed 35°. The solution is subsequently stirred for 20 hours at room temperature. The methanol is thereupon evaporated off in vacuo; the aqueous phase remaining behind is extracted twice with 500 ml of chloroform each time, the chloroform solution dried over sodium sulphate, filtered, and concentrated by evaporation. The 1-methyl-4-(5-chloro-2-benzofuranyl)-1,2,3,6-tetrahydropyridine obtained is recrystallised from hexane, and then melts at 108°-118°. The hydrochloride prepared therefrom with a solution of hydrogen chloride in ethyl acetate melts, after recrystallisation from ethyl acetate, at 266°.

In an analogous manner there is obtained, with the use of 78.2 g of 1-methyl-4-(5-bromo-2-benzofuranyl)-pyridinium-iodide: 1-methyl-4-(5-bromo-2-benzofuranyl)-1,2,3,6-tetrahydropyridine, M.P. 129°.

The starting material can be prepared in the following manner:

(a) 210 g of 5-chlorosalicylaldehyde, 220 g of 4-(chloromethyl)-pyridine-hydrochloride, 750 g of potassium carbonate and 3.3 g of potassium iodide are heated in 2 liters of dimethylformamide, with stirring, for 20 hours at 80°. The solution is thereupon filtered under suction, and the filter residue washed with 1 liter of chloroform. The combined filtrates are concentrated in vacuo, and the residue is dissolved in 1 liter of chloroform. The organic phase is washed twice with 1 liter of 2 N sodium hydroxide solution each time, and then with 1 liter of water; it is subsequently dried over sodium sulphate, filtered, and concentrated by evaporation. The resulting crude 2-[(4-pyridyl)-methoxy]-5-chlorobenzaldehyde is further processed without purification.

(b) 272 g of 2-[(4-pyridyl)-methoxy]-5-chlorobenzaldehyde is heated for 30 minutes under nitrogen at 300°. After cooling, the residue is dissolved in a small amount of methylene chloride, and the solution chromatographed through 2 kg of aluminium oxide (activity II, neutral). The first fraction, eluted with 5 liters of methylene chloride, is 4-(5-chloro-2-benzofuranyl)-pyridine. After recrystallisation from ethanol, the compound melts at 132°-133°. The hydrochloride prepared therefrom with a solution of hydrogen chloride in ethyl acetate melts, after recrystallisation from ethyl acetate, at 265°.

(c) 142 g of 4-(5-chloro-2-benzofuranyl)pyridine is dissolved in 450 ml of methanol, and the solution stirred with 300 ml of methyl iodide for 15 hours at 40°-45°. The solution is then cooled to 0°, and the precipitated salt filtered off with suction. The filter residue is subsequently washed with 500 ml of isopropanol. After recrystallisation from isopropanol, the resulting 1-methyl-4-(5-chloro-2-benzofuranyl)-pyridinium-iodide melts at 258°-260°.

Analogously to (a) there are obtained, using 269 g of 5-bromosalicylaldehyde: crude 2-[(4-pyridyl)-methoxy]-5-bromosalicylaldehyde; and further, starting with 320 g of this crude product, analogously to (b): 4-(5-bromo-2-benzofuranyl)-pyridine, M.P. 156°-158°;

and, finally, analogously to (c), from 168 g of 4-(5-bromo-2-benzofuranyl)-pyridine: 1-methyl-4-(5-bromo-2-benzofuranyl)-pyridinium-iodide, M.P. 266°–270°.

EXAMPLE 13

A solution of 40 g of sodium borohydride in 100 ml of water is added dropwise, with stirring and external cooling, to a solution of 44.3 g of 1-methyl-4-(5-methoxy-2-benzofuranyl)-pyridinium-iodide in 350 ml of methanol, the manner of addition being such that the reaction temperature does not exceed 35°. The solution is subsequently stirred for 20 hours at room temperature. The methanol is then evaporated off in vacuo, the aqueous phase remaining behind extracted twice with 500 ml of chloroform each time, the chloroform solution dried over sodium sulphate, filtered, and concentrated by evaporation. The resulting 1-methyl-4-(5-methoxy-2-benzofuranyl)-1,2,3,6-tetrahydropyridine is recrystallised from cyclohexane, and then melts at 99°–101°. The hydrochloride prepared therefrom with a solution of hydrogen chloride in ethyl acetate melts, after recrystallisation from ethyl acetate, at 238°.

In an analogous manner there are obtained, starting with 47.9 g of 1-methyl-4-(5,6-dimethoxy-2-benzofuranyl)-pyridinium-iodide: 1-methyl-4,5,6-dimethoxy-2-benzofuranyl-1,2,3,6-tetrahydropyridine, M.P. 139°–141°, and the hydrochloride thereof, M.P. 234°–236°.

The starting materials can be prepared as follows:

(a) 29.4 g of 4-(5-methoxy-2-benzofuranyl)-pyridine [cp. Example 2 (a)] is dissolved in 250 ml of methanol, and the solution stirred with 100 ml of methyl iodide for 15 hours at 40°–45°. The solution is then cooled to 20°, stirred with active charcoal, and filtered through purified diatomaceous earth. The filtrate is concentrated in vacuo, and the residue recrystallised from isopropanol. The resulting 1-methyl-4-(5-methoxy-2-benzofuranyl)-pyridinium-iodide melts at 210°–212°.

In an analogous manner there is obtained, with the use of 33.3 g of 4-(5,6-dimethoxy-2-benzofuranyl)-pyridine (cp. Example 3b): 1-methyl-4-(5,6-dimethoxy-2-benzofuranyl)-pyridinium-iodide, M.P. 268°–270°.

EXAMPLE 14

A solution of 40.0 g of sodium borohydride in 160 ml of water is added dropwise, with stirring and external cooling, to a solution of 91.0 g of 1-methyl-4-(7-methoxy-2-benzofuranyl)-pyridinium-iodide in 1500 ml of methanol, the manner of addition being such that the reaction temperature does not exceed 35°. The solution is subsequently stirred for 20 hours at room temperature. The methanol is then evaporated off in vacuo, the aqueous phase remaining behind extracted twice with 500 ml of methylene chloride each time, the methylene chloride solution dried over sodium sulphate, filtered, and concentrated by evaporation. The residue obtained is dissolved in a little methylene chloride, and chromatographed through 900 g of aluminium oxide (activity II, neutral). The first fraction, eluted with 3 liters of methylene chloride, is 1-methyl-4-(7-methoxy-2-benzofuranyl)-1,2,3,6-tetrahydropyridine. After recrystallisation from pentane, the free base melts at 89°–92°. The hydrochloride prepared therefrom with a solution of hydrogen chloride in ethyl acetate melts, after recrystallisation from ethyl acetate, at 246°–248°.

The starting material can be prepared in the following manner:

(a) 60 g of 4-(7-methoxy-2-benzofuranyl)-pyridine (cp. Example 3(b)) is dissolved in 750 ml of methanol, and stirred with 150 ml of methyl iodide for 15 hours at 40°–45°. The solution is thereupon cooled to 0°, and the crystals are filtered off with suction. The 1-methyl-4-(7-methoxy-2-benzofuranyl)-pyridinium-iodide thus obtained melts, after recrystallisation from ethanol, at 219°.

EXAMPLE 15

A solution of 60 g of sodium borohydride in 150 ml of water is added dropwise, with stirring and external cooling, to a solution of 125 g of 1-methyl-4-(5-methyl-2-benzofuranyl)-pyridinium-iodide in 750 ml of methanol, the manner of addition being such that the reaction temperature does not exceed 35°. The solution is subsequently stirred for 20 hours at room temperature. The methanol is then evaporated off in vacuo; the aqueous phase remaining behind is extracted twice with 500 ml of chloroform each time, the chloroform solution dried over sodium sulphate, filtered, and concentrated by evaporation. The resulting 1-methyl-4-(5-methyl-2-benzofuranyl)-1,2,3,6-tetrahydropyridine is recrystallised from diisopropyl ether, and then melts at 102°. The hydrochloride prepared therefrom with a solution of hydrogen chloride in ethyl acetate melts, after recrystallisation from ethyl acetate; at 243°.

The starting material can be prepared in the following manner from the compound of Example 4(a):

(a) 80 g of 4-(5-methyl-2-benzofuranyl)-pyridine is dissolved in 150 ml of methanol, and stirred with 150 ml of methyl iodide for 15 hours at 40°–45°. The solution is then cooled to 0°, and the precipitated salt filtered off with suction. The filter residue is washed with 500 ml of ethanol. After recrystallisation from methanol, the resulting 1-methyl-4-(5-methyl-2-benzofuranyl)-pyridinium iodide melts at 198°–200°.

EXAMPLE 16

A solution of 27.0 g of sodium borohydride in 110 ml of water is added dropwise, with stirring and external cooling, to a solution of 65.5 g of 1-methyl-4-(naphtho [2,1-b]furan-2-yl)-pyridinium-iodide in 900 ml of methanol, the manner of addition being such that the reaction temperature does not exceed 30°. The solution is subsequently stirred for 15 hours at room temperature. The methanol is then evaporated off in vacuo; the aqueous phase remaining behind is extracted twice with 500 ml of chloroform each time, the chloroform solution dried over sodium sulphate, filtered, and concentrated by evaporation. The oil thus obtained is dissolved in 150 ml of methylene chloride, and chromatographed through 1 kg of aluminium oxide (activity II, neutral). The first fractions, eluted with 2 liters of methylene chloride, contain 1-methyl-4-naphtho-[2,1-b]furan-2-yl)-1,2,3,6-tetrahydropyridine. The free base is recrystallised from hexane, and then melts at 120°–122°. The hydrochloride prepared therefrom with a solution of hydrogen chloride in ethyl acetate melts at 277° after recrystallisation from ethyl acetate.

The starting material can be prepared in the following manner:

(a) 83.4 g of 2-hydroxy-naphthaldehyde, 79.3 g of 4-(chloromethyl)-pyridine-hydrochloride, 300 g of potassium carbonate and 2.5 g of potassium iodide are heated in 800 ml of dimethylformamide, with stirring, for 20 hours at 100°. The solution is then filtered with suction, and the filter residue washed with 1 liter of chloroform. The combined filtrates are concentrated in vacuo, and the residue is dissolved in 1 liter of chloroform. The organic phase is firstly washed twice with 1 liter of 2 N sodium hydroxide solution each time and then once with 1 liter of water; it is dried over sodium sulphate, filtered, and concentrated by evaporation. The crude 2-[(4-pyridyl)-methoxy]-1-naphthaldehyde is further processed without purification.

(b) 93.0 g of 2-[(4-pyridyl)-methoxy]-1-naphthaldehyde is heated under nitrogen for 30 minutes at 300°. After cooling, the residue is dissolved in a little methylene chloride, and chromatographed through 2 kg of aluminium oxide (activity II, neutral). The first fraction, eluted with 3 liters of methylene chloride, is 4-(naphtho[2,1-b]furan-2-yl)-pyridine. After recrystallisation from ethyl acetate, the compound melts at 137°–139°. The hydrochloride prepared therefrom with a solution of hydrogen chloride in ethyl acetate melts at 295°–300° after recrystallisation from ethyl acetate.

(c) 51.0 g of 4-(naphtho[2,1-b]furan-2-yl)-pyridine is dissolved in 750 ml of methanol, and the solution stirred with 100 ml of methyl iodide for 20 hours at 40°–45°. The solution is afterwards cooled to 0°, and the precipitated salt filtered off under suction, and subsequently washed with 150 ml of isopropanol. After recrystallisation from isopropanol, the resulting 1-methyl-4-(naphtho[2,1-b]furan-2-yl)-pyridinium-iodide melts at 310°–315° (with decomposition).

EXAMPLE 17

A solution of 75 g of sodium borohydride in 150 ml of water is added dropwise, with stirring and external cooling, to a solution of 75 g of 1-benzyl-4-(2-benzofuranyl)-pyridinium-bromide in 500 ml of methanol, the manner of addition being such that the reaction temperature does not exceed 35°. The solution is subsequently stirred for 20 hours at room temperature. The methanol is then evaporated off in vacuo; the aqueous phase remaining behind is extracted twice with 500 ml of chloroform each time, the chloroform solution is dried over sodium sulphate, filtered, and concentrated by evaporation. The resulting 1-benzyl-4-(2-benzofuranyl)-1,2,3,6-tetrahydropyridine melts at 138° after recrystallisation from diethyl ether. The hydrochloride prepared therefrom with a solution of hydrogen chloride in methyl acetate melts at 237°–238° after recrystallisation from acetone/isopropanol.

The starting material can be prepared as follows:

(a) 99 g of 4-(2-benzofuranyl)-pyridine [cp. Example 1(b)] is dissolved in 1600 ml of methanol, and the solution refluxed with 120 g of benzyl bromide for 15 hours. The solution is then cooled to 20°, stirred for 10 minutes with 50 g of active charcoal, and filtered through purified diatomaceous earth. The filtrate is concentrated in vacuo and the residue recrystallised from acetone. The resulting 1-benzyl-4-(2-benzofuranyl)-pyridinium-bromide melts at 213°–215°.

EXAMPLE 18

A solution of 70.0 g of sodium borohydride in 150 ml of water is added dropwise, with stirring and external cooling, to a solution of 100.0 g of 1-methyl-4-(3-methyl-2-benzofuranyl)-pyridinium iodide in 500 ml of methanol, the manner of addition being such that the reaction temperature does not exceed 35°. The solution is then stirred for 20 hours at room temperature. The methanol is afterwards evaporated off in vacuo, the aqueous phase remaining behind extracted twice with 500 ml of chloroform each time, the chloroform solution dried over sodium sulphate, filtered, and concentrated by evaporation. The resulting residue is dissolved in a little methylene chloride, and chromatographed through 1000 g of aluminium oxide (activity II, neutral). The first fraction, eluted with 1 liter of methylene chloride, is 1-methyl-4-(3-methyl-2-benzofuranyl)-1,2,3,6-tetrahydropyridine. The compound melts at 56°–58° after recrystallisation from pentane. The hydrochloride prepared therefrom with a solution of hydrogen chloride in methyl acetate melts, after recrystallisation from ethyl acetate, at 284°–286°.

The starting material can be prepared in the following manner:

(a) 64.0 g of o-hydroxyacetophenone, 64.6 g of 4-(chloromethyl)-pyridine-hydrochloride, 250 g of sodium carbonate and 3 g of potassium iodide are heated in 1 liter of dimethylformamide, with stirring, for 20 hours at 120°. The solution is then filtered with suction, and the filter residue washed with 500 ml of dimethylformamide. The combined filtrates are concentrated in vacuo, and the residue dissolved in 1 liter of chloroform. The organic phase is firstly washed twice with 1 liter of 2 N sodium hydroxide solution each time, and then once with 1 liter of water; it is dried over sodium sulphate, filtered, and concentrated by evaporation. The crude 2-[(4-pyridyl)-methoxy]-acetophenone is further processed without additional purification.

(b) 80 g of 2-[(4-pyridyl)-methoxy]-acetophenone is heated for 40 minutes at 300° under nitrogen. After cooling, the residue is dissolved in a little methylene chloride, and chromatographed through 1000 g of aluminium oxide (activity II, neutral). The first fraction, eluted with 1.5 liters of methylene chloride, is 4-(3-methyl-2-benzofuranyl)-pyridine. The compound melts at 55°–57° after recrystallisation from hexane. The hydrochloride prepared from this compound with a solution of hydrogen chloride in ethyl acetate melts, after recrystallisation from ethyl acetate, at 280°.

(c) 56.0 g of 4-(3-methyl-2-benzofuranyl)-pyridine is dissolved in 350 ml of methanol, and the solution stirred with 75 ml of methyl chloride for 20 hours at 40°–45°. The solution is thereupon cooled to 0°, and the precipitated salt filtered off with suction. The filter residue is subsequently washed with ethanol. After recrystallisation from methanol, the resulting 1-methyl-4-(3-methyl-2-benzofuranyl)-puridinium-iodide melts at 236°–238°.

EXAMPLE 19

112 g of 1-methyl-4-(4-(5-chloro-2-benzofuranyl)-1,2,3,6-tetrahydropyridine (cp. Example 12) is dissolved in 2.3 liters of methanol, and the solution hydrogenated in the presence of 11 g of platinum oxide at a temperature of between 20° and 30° and under normal pressure. After 9 hours, 9.87 liters of hydrogen has been absorbed, this amount corresponding exactly to the theoretical amount that can be absorbed. Hydrogenation is terminated, the catalyst filtered off, and the filtrate concentrated in vacuo. The residue is dissolved in a little chloroform, and the solution chromatographed through 600 g of aluminium oxide (activity II, neutral). The first fraction, eluted with 2 liters of chloroform, is 1-methyl-4-(5-chloro-2-benzofuranyl)-piperidine. This melts at 107° after recrystallisation from hexane. The hydrochloride prepared from a solution of the base with a solution of hydrogen chloride in ethyl acetate melts at 260°.

In an analogous manner there are obtained, starting with 132 g of 1-methyl-4-(5-bromo-2-benzofuranyl)-1,2,3,6-tetrahydropyridine (cp. Example 12): 1-methyl-4-(5-bromo-2-benzofuranyl)-piperidine, M.P. 116°–119°, and the hydrochloride thereof, M.P. 272°–275°.

EXAMPLE 20

22.0 g of 1-methyl-4-(5-methoxy-2-benzofuranyl)-1,2,3,6-tetrahydropyridine (cp. Example 13) is dissolved in 220 ml of methanol, and the solution hydrogenated in the presence of 4 g of palladium charcoal catalyst (5% Pd) at a temperature of 40°–50° and under normal pressure. Hydrogenation is terminated after 11 hours, the catalyst filtered off, and the filtrate concentrated in vacuo. The residue is dissolved in a little chloroform, and the solution chromatographed through 400 g of aluminium oxide (activity II, neutral). The first fraction, eluted with 2 liters of chloroform, is 1-methyl-4-(5-methoxy-2-benzofuranyl)-piperidine. This melts at 68° after recrystallisation from hexane. The hydrochloride prepared from a solution of the base with a solution of hydrogen chloride in ethyl acetate melts at 282°–284°.

In an analogous manner there are obtained by hydrogenation of 24.7 g of 1-methyl-4-(5,6-dimethoxy-2-benzofuranyl)-1,2,3,6-tetrahydropyridine: 1-methyl-4-(5,6-dimethoxy-2-benzofuranyl)-piperidine, M.P. 73°–75°, and from this the hydrocloride, M.P. 228°–231°.

EXAMPLE 21

24.2 g of 1-methyl-4-(7-methoxy-2-benzofuranyl)-1,2,3,6-tetrahydropyridine (cp. Example 14) is dissolved in 200 ml of methanol, and the solution hydrogenated in the presence of 4 g of palladium charcoal catalyst (5% Pd) at a temperature of 40°–50° and under normal pressure. Hydrogenation is terminated after 15 hours, the catalyst filtered off, and the filtrate concentrated in vacuo. The resulting 1-methyl-4-(7-methoxy-2-benzofuranyl)-piperidine melts at 76°–78° after recrystallisation from pentane. The hydrochloride prepared from a solution of hydrogen chloride in ethyl acetate melts at 172°–173°.

EXAMPLE 22

28.5 g of 1-methyl-4-(5-methyl-2-benzofuranyl)-1,2,3,6-tetrahydropyridine (cp. Example 15) is dissolved in 150 ml of methanol, and the solution hydrogenated in the presence of 60 g of Raney nickel at a temperature of between 90° and 95° and under an initial pressure of 100 bars. The amount of hydrogen absorbed after 15 hours is precisely the theoretical amount. Hydrogenation is then terminated, the catalyst filtered off, and the filtrate concentrated by evaporation. The resulting 1-methyl-4-(5-methyl-2-benzofuranyl)-piperidine melts at 88°–90° after recrystallisation from hexane. The hydrochloride prepared from a solution of the base with a solution of hydrogen chloride in ethyl acetate melts at 186°–189°.

EXAMPLE 23

26.0 g of 1-methyl-4-(naphthol[2,1-b]furan-2-yl)-1,2,3,6-tetrahydropyridine is dissolved in 300 ml of methanol, and the solution hydrogenated in the presence of 3 g of palladium charcoal catalyst (5% Pd) at a temperature of between 40° and 50° and under normal pressure. After 2 hours, 2.27 liters of hydrogen chloride has been absorbed, corresponding exactly to the theoretical amount of absorbed hydrogen. Hydrogenation is then terminated, the catalyst filtered off, and the filtrate concentrated in vacuo. The residue is 1-methyl-4-)naphtho[2,1-b]furan-2-yl)-piperidine. This melts at 83°–85° after recrystallisation from pentane. The hydrochloride prepared from a solution of the base with a solution of hydrogen chloride in ethyl acetate melts at 243°.

The starting material is prepared according to Example 16.

EXAMPLE 24

77.5 g of 1-benzyl-4-(2-benzofuranyl)-1,2,3,6-tetrahydro-pyridine (cp. Example 17) is dissolved in 200 ml of methanol, and the solution, after addition of 53 ml of 4.56% (W/V) methanolic hydrogen chloride solution (corresponding to one equivalent of HCl), hydrogenated at a temperature of between 20° and 30° and under normal pressure. The amount of hydrogen absorbed after 17 hours is 1.36 liters, an amount corresponding to the theoretical amount of hydrogen absorption for one equivalent. Hydrogenation is then terminated, the catalyst filtered off, and the filtrate concentrated in vacuo. The residue is 1-benzyl-4-(2-benzofuranyl)-piperidine. This melts at 77°–79° after recrystallisation from hexane. The hydrochloride prepared from a solution of the base with a solution of hydrogen chloride in ethyl acetate melts at 217°–218°.

EXAMPLE 25

50.5 g of 1-methyl-4-(3-methyl-2-benzofuranyl)-1,2,3,6-tetrahydropyridine (cp. Example 18) is dissolved in 500 ml of methanol, and the solution hydrogenated in the presence of 1 g of platinum oxide at a temperature of between 20° and 30° and under normal pressure. The amount of hydrogen absorbed after 31 hours is 4.98 liters, and this corresponds exactly to the theoretical amount of hydrogen. Hydrogenation is then terminated, the catalyst filtered off, and the filtrate concentrated in vacuo. The residue is dissolved in methylene chloride, and the solution chromatographed through 800 g of aluminium oxide (neutral, activity II). The first fraction, eluted with 3 liters of methylene chloride, is 1-methyl-4-(3-methyl-2-benzofuranyl)-piperidine. The hydrochloride prepared from a solution of the base with a solution of hydrogen chloride in ethyl acetate melts at 228°–230°.

EXAMPLE 26

15.0 g of 1-methyl-4-(5-chloro-2-benzofuranyl)-piperidine (see Example 19) is dissolved in 150 ml of toluene, and 40.0 g of chloroformic acid ethyl ester added to the solution. The solution is refluxed for 15 hours with stirring, whereby during the first hour, to effect a more rapid removal of the liberated methyl chloride, a small amount of toluene is distilled off and thereafter provision made for complete refluxing of the toluene. The solution is subsequently cooled to 20°, filtered with suction, and the filter residue then washed with 800 ml of toluene. The combined filtrates are successively washed with 500 ml of water, 1 liter of water, 1 liter of a 10% solution of methanesulphonic acid in water, 1 liter of water, 500 ml of 2 N sodium hydroxide, and 500 ml of water; they are then dried over sodium sulphate, filtered, and concentrated by evaporation. The resulting crude 4-(5-chloro-2-benzofuranyl)-1-piperidine-carboxylic acid ethyl ester is further processed without purification.

11.5 g of 4-(5-chloro-2-benzofuranyl)-1-piperidinecarboxylic acid ethyl ester is dissolved in 75 ml of ethylene glycol. After the addition of 50 ml of a 50% aqueous potassium hydroxide solution, the formed cloudy solution is heated, with vigorous stirring, for 15 hours at 160°; the reaction solution is thereupon cooled to 20°, and extracted twice with 500 ml of ethyl acetate each time. The organic phases are washed five times with 1 liter of water each time, dried over sodium sulphate, filtered, and concentrated by evaporation. The residue is dissolved in 300 ml of a 10% solution of methanesulphonic acid in water, and the acid solution extracted with ether. The aqueous solution is then adjusted by addition of 10% sodium hydroxide solution to have a pH value of 12, and extracted with 1 liter of chloroform. The chloroform solution is dried with sodium sulphate, filtered, and concentrated by evaporation to obtain crude 4-(5-chloro-2-benzofuranyl)-piperidine. The free base melts at 77°-78° after recrystallisation from hexane. The hydrochloride is prepared with hydrogen chloride in ethyl acetate, and recrystallised from ethyl acetate, whereupon its melts at 252°-254°.

EXAMPLE 27

Analogously to Example 26 there is obtained, starting with 14.4 g of 1-methyl-4-(5-methyl-2-benzofuranyl)-1,2,3,6-tetrahydropyridine (see Example 15): crude 4-(5-methyl-2-benzofuranyl)-3,6-dihydro-1(2H)-pyridinecarboxylic acid ethyl ester, which can be used direct for hydrolysis. A sample of the substance recrystallised from pentane melts at 85°.

The above ester is hydrolysed analogously to Example 26, whereby 4-(5-methyl-2-benzofuranyl)-1,2,3,6-tetrahydropyridine is obtained, which is converted into its hydrochloride analogously to Example 26.

Likewise analogously to Example 26, there are obtained:

starting with 14.9 g of 1-methyl-4-(5-chloro-2-benzofuranyl)-1,2,3,6-tetrahydropyridine (see Example 12): crude 4-(5-chloro-2-benzofuranyl)-3,6-dihydro-1(2H)-pyridinecarboxylic acid ethyl ester, and from this: 4-(5-chloro-2-benzofuranyl)-1,2,3,6-tetrahydropyridine and its hydrochloride;

starting with 12.3 g of 1-methyl-4-(2-benzofuranyl)-1,2,3,6-tetrahydropyridine: crude 4-(2-benzofuranyl)-3,6-dihydro-1(2H)-pyridinecarboxylic acid ethyl ester, and from this: 4-(2-benzofuranyl)-1,2,3,6-tetrahydropyridine and its hydrochloride; starting with 14.6 g of 1-methyl-4-(5-methoxy-2-benzofuranyl)-1,2,3,6-tetrahydropyridine (see Example 13): crude 4-(5-methoxy-2-benzofuranyl)-3,6-dihydro-1(2H)-pyridinecarboxylic acid ethyl ester, and from this. 4-(5-methoxy-2-benzofuranyl)-1,2,3,6-tetrahydropyridine and its hydrochloride;

starting with 14.6 g of 1-methyl-4-(7-methoxy-2-benzofuranyl)-1,2,3,6-tetrahydropyridine (see Example 14): crude 4-(7-methoxy-2-benzofuranyl)-3,6-dihydro-1(2H)-pyridinecarboxylic acid ethyl ester, and from this: 4-(7-methoxy-2-benzofuranyl)-1,2,3,6-tetrahydropyridine and its hydrochloride;

starting with 14.4 g of 1-methyl-4-(3-methyl-2-benzofuranyl)-1,2,3,6-tetrahydropyridine (see Example 18): crude 4-(3-methyl-2-benzofuranyl)-3,6-dihydro-1(2H)-pyridinecarboxylic acid ethyl ester, and from this: 4-(3-methyl-2-benzofuranyl)-1,2,3,6-tetrahydropyridine and its hydrochloride;

starting with 14.5 g of 1-methyl-4-(3-methyl-2-benzofuranyl)-piperidine (see Example 25): crude 4-(3-methyl-2-benzofuranyl)-1-piperidinecarboxylic acid ethyl ester, and from this: 1-(3-methyl-2-benzofuranyl)-piperidine and its hydrochloride.

EXAMPLE 28

12.0 g of 1-methyl-4-(naphtho[2,1-b]furan-2-yl)-piperidine (see example 23) is dissolved in 150 ml of toluene, and an addition slowly made dropwise, under a strong flow of nitrogen for the more rapid removal of the liberated methyl chloride, of 40.0 g of chloroformic acid ethyl ester. The solution is then refluxed for 20 hours, cooled, filtered with suction, and the filter residue subsequently washed with 500 ml of toluene. The combined filtrates are successively washed with 500 ml of water, 1 liter of a 10% solution of methanesulphonic acid in water, 500 ml of water, 500 ml of 2 N sodium hydroxide solution and 500 ml of water; they are then dried over sodium sulphate, filtered, and concentrated by evaporation. The 4-(naphtho[2,1-b]furan-2-yl)-1-piperidinecarboxylic acid ethyl ester remaining behind melts at 89°-92° after recrystallisation from pentane.

7.8 g of 4-(naphtho[2,1-b]furan-2-yl)-1-piperidinecarboxylic acid ethyl ester is dissolved in 60 ml of ethylene glycol. After the addition of 40 ml of a 50% aqueous potassium hydroxide solution, the formed cloudy solution is heated, with vigorous stirring, for 15 hours at 160°. The reaction solution is thereupon cooled to 20° and extracted twice with 500 ml of ethyl acetate. The organic phases are washed five times with 1 liter of water each time, dried over sodium sulphate, filtered, and concentrated by evaporation. The residue is dissolved in 400 ml of 2 N hydrochloric acid, and the acid solution extracted with toluene. The aqueous solution is then adjusted by addition of 10% sodium hydroxide solution to have a pH value of 12, and extracted with 1 liter of chloroform. The chloroform solution is dried with sodium sulphate, filtered, and concentrated by evaporation to obtain crude 4-(naphtho[2,1-b]furan-2-yl)-piperidine. The hydrochloride is prepared with hydrogen chloride in ethyl acetate, and recrystallised from ethyl acetate, whereupon it melts at 225°.

In an analogous manner there are obtained: starting with 15.8 g of 1-methyl-4-(naphtho[2,1-b]furan-2-yl)-1,2,3,6-tetrahydropyridine (see Example 16): crude 4-(naphtho[2,1-b]furan-2-yl)-3,6-dihydro-1(2H)pyridinecarboxyl acid ethyl ester, and from this: 4-(naphtho[2,1-b]furan-2-yl)-1,2,3,6-tetrahydropyridine.

EXAMPLE 29

88.8 g of 1-benzyl-4-(2-benzofuranyl)-1,2,3,6-tetrahydropyridine (cp. Example 17) is dissolved in 900 ml of methanol, and the solution hydrogenated in the presence of 9.0 g of palladium charcoal (5% Pd) at a temperature of between 30° and 40° and under normal pressure. After 22 hours, 12.2 liters of hydrogen have been absorbed, which corresponds exactly to the theoretical amount of hydrogen absorption for 2 equivalents. Hydrogenation is terminated, the catalyst filtered off, and the filtrate concentrated in vacuo. The residue is fractionally distilled in high vacuum. The fraction distilling at 108°-110° and 0.06 Torr is 4-(2-benzofuranyl)-piperidine, which is identical to the compound described in Example 1.

EXAMPLE 30

A solution of 6.0 g of sodium borohydride in 25 ml of water is added dropwise, with stirring and external cooling, to a solution of 6.0 g of 1-(3-oxobutyl)-4-(2-benzofuranyl)-piperidine (cp. Example 8), the manner of addition being such that the reaction temperature does not exceed 30°. The mixtuure is subsequently stirred for 15 hours at room temperature. The methanol is then evaporated off in vacuo, the aqueous phase remaining behind extracted twice with 250 ml of chloroform each time, the chloroform solution dried over sodium sulphate, filtered, and concentrated by evaporation. The residue is dissolved in 500 ml of 2 N hydrochloric sacid, and the acid solution washed with ether. The aqueous solution is subsequently adjusted by addition of 10% sodium hydroxide solution to have a pH value of 12, and extracted with 1 liter of chloroform. The chloroform solution is dried with sodium sulphate, filtered, and concentrated by evaporation to obtain crude 1-(3-hydroxybutyl)-4-(2-benzofuranyl)-piperidine (4-(2-benzofuranyl)-α-methyl-1-piperidine-propanol). The hydrochloride of this is prepared with hydrogen chloride in ethyl acetate, and recrystallised from ethyl acetate, whereupon it melts at 194°–195°.

EXAMPLE 31

A solution of 45 g of sodium borohydride in 190 ml of water is added dropwise, with stirring and external cooling, to a solution of 99 g of 1-methyl-4-(5,6-dimethylbenzofuranyl)-pyridinium-iodide in 1500 ml of methanol, the manner of addition being such that the reaction temperature does not exceed 35°. The solution is subsequently stirred for 15 hours at room temperature. The methanol is thereupon evaporated off in vacuo; the aqueous phase remaining behind is extracted twice with 750 ml of chloroform each time, the chloroform solution dried over sodium sulphate, filtered, and concentrated by evaporation. The oily residue is recrystallised from cyclohexane, whereby the 1-methyl-4-(5,6-dimethyl-2-benzofuranyl)-1,2,3,6-tetrahydropyridine, M.P. 124°–126°, is obtained. The hydrochloride prepared therefrom with a solution of hydrogen chloride in ethyl acetate melts, after recrystallisation from ethyl acetate. at 231°–233°.

In an analogous manner there is obtained
from 99 g of 1-methyl-4-(4,7-dimethyl-2-benzofuranyl)-pyridinium-iodide: 1-methyl-4-(4,7-dimethyl-2-benzofuranyl)-1,2,3,6-tetrahydropyridine, M.P. 69°–71°, hydrochloride M.P. 281°–283°;

from 99 g of 1-methyl-4-(5,7-dimethyl-2-benzofuranyl)-pyridinium-iodide: 1-methyl-4-(5,7-dimethyl-2-benzofuranyl)-1,2,3,6-tetrahydro-pyridine, M.P. 99°–102°, hydrochloride M.P. 250°–252°;

from 110 g of 1-methyl-4-[5-(trifluoromethyl)-2-benzofuranyl]-pyridinium-iodide: 1-methyl-4-[5-(trifluoromethyl)-2-benzofuranyl]-1,2,3,6-tetrahydropyridine and its hydrochloride;

from 102 g of 1-methyl-4-[5,6-(trimethylene)-2-benzofuranyl]-pyridinium-iodide: 1-methyl-4-[5,6-(trimethylene)-2-benzofuranyl]-1,2,3,6-tetrahydropyridine and its hydrochloride.

The starting materials can be prepared in the following manner:

(a) 58.5 g of 4,5-dimethylsalicylaldehyde, 64.0 g of 4-(chloromethyl)-pyridine-hydrochloride, 240 g of potassium carbonate and 2.0 g of potassium iodide are heated in 500 ml of dimethylformamide, with stirring for 20 hours at 150°–170°. The reaction mixture is thereupon filtered under suction, and the filter residue washed with 1 liter of chloroform. The combined filtrates are concentrated in vacuo, and the residue is dissolved is dissolved in 150 ml of methylene chloride, and the solution chromatographed through 2000 g of aluminium oxide (activity II, neutral). The first fraction, eluted with 2.8 liters of methylene chloride, is 4-(4,5-dimethyl-2-benzofuranyl)-pyridine. After recrystallisation from hexane, the compound melts at 168 –170°. The hydrochloride prepared therefrom with a solution of hydrogen chloride in ethyl acetate melts, after recrystallisation from ethyl acetate, at 278°–280°.

Analogously there are obtained:
from 58.5 g of 3,6-dimethylsalicylaldehyde: 4-(4,7-dimethyl-2-benzofuranyl)-pyridine, M.P. 78°–80°, hydrochloride-hydrate, M.P. 266°–269°;

from 58.5 g of 3,5-dimethylsalicylaldehyde; 4-(5,7-dimethyl-2-benzofuranyl)-pyridine, M.P. 107°–109°, hydrochloride M.P. 285°;

from 74.2 g 5-(trifluoromethyl)-salicylaldehyde (α,α,α-trifluoro-2,5-cresotaldehyde): 4-[5-(trifluoromethyl)-2-benzofuranyl]-pyridine, and from 62.8 g 4,5-(trimethylene)-salicylaldehyde (6-hydroxy-5-indanecarboxaldehyde, cp. J. Amer. Chem. Soc. 77, 2466–75): 4-[5,6-trimethylene)-2-benzofuranyl]-pyridine, U.P. 90–92;

(b) 79.0 g of 4-(5,6-dimethyl-2-benzofuranyl)-pyridine is dissolved in 750 ml of methanol and stirred with 100 ml of methyl iodide for 20 hours at 40°–45°. The solution is then cooled to −20°, and the precipitated salt is filtered off with suction and subsequently washed with 150 ml of isopropanol. After recrystallisation from isopropanol, the resulting 1-methyl-4-(5,6-dimethyl-2-benzofuranyl)-pyridinium-iodide melts at 219°–221°.

Analogously there are obtained:
from 79.0 g 4-(4,7-dimethyl-2-benzofuranyl)-pyridine: 1-methyl-4-(4,7-dimethyl-2-benzofuranyl)-pyridinium-iodide, M.P. 316°–320°;

from 79.0 g of 4-(5,7-dimethyl-2-benzofuranyl)-pyridine: 1-methyl-4-(5,7-dimethyl-2-benzofuranyl)-pyridinium-iodide, M.P. 268°–270°;

from 93.2 g 4-[5-(trifluoromthyl)-2-benzofuranyl]-pyridine: 1-methyl-4-[5-(trifluoromethyl)-2-benzofuranyl]-pyridinium-iodide, and from 83.4 g of 4-[5,6-(trimethylene)-2-benzofuranyl]-pyridine: 1-methyl-4-[5,6-(trimethylene)-2-benzofuranyl]-pyridinium-iodide, M.P. 194°–197°.

EXAMPLE 32

139 g of 1-methyl-4-(5,6-dimethyl-2-benzofuranyl)-1,2,3,6-tetrahydropyridine (cp. Example 31) is dissolved in 1500 ml of methanol, and the solution hydrogenated in the presence of 14 g of palladium charcoal catalyst (5% Pd) at a temperature of between 20° and 25° and under normal pressure. After 8 hours, the theoretical amount of 13 liters of hydrogen has been absorbed. Hydrogenation is terminated, the catalyst filtered off, and the filtrate concentrated in vacuo. The crude 1-methyl-4-(5,6-dimethyl-2-benzofuranyl)-piperidine remaining behind is recrystallised from cyclohexane, and then melts at 122°–124°. The hydrochloride prepared from a solution of the base with a solution of hydrogen chloride in ethyl acetate melts at 205°–207°.

In an analogous manner there are obtained, starting with the same amount
of 1-methyl-4-(4,7-dimethyl-2-benzofuranyl)-1,2,3,6-tetrahydropyridine (cp. Example 31): 1-methyl-4-(4,7-dimethyl-2-benzofuranyl)-piperidine, and its hydrochloride, which melts at 242°;

of 1-methyl-4-(5,7-dimethyl-2-benzofuranyl)-1,2,3,6-tetrahydropyridine (cp. Example 31): 1-methyl-4-(5,7-dimethyl-2-benzofuranyl)-piperidine and its hydrochloride which melts at 210°–212°;

There likewise are obtained, by hydrogenation in the presence of 8 g of the catalyst in 800 ml of methanol until 5 liters of hydrogen are absorbed, but in all other respects analogously, the following compounds;

from 62.2 g of 1-methyl-4-[5-(trifluoromethyl)-2-benzofuranyl]-1,2,3,6-tetrahydropyridine [cp. Example 31]: 1-methyl-4-(trifluoromethyl)-2-benzofuranyl]-piperidine and its hydrochloride, and from 56.0 g of 1-methyl-4-[5,6-(trimethylene)-2-benzofuranyl]-1,2,3,6-tetrahydropiridine [cp. Example 31]: 1-methyl-4-[5,6-(trimethylene)-2-benzofuranyl]-piperidine and its hydrochloride.

EXAMPLE 33

43 g of 1-methyl-4-(5,6-dimethyl-2-benzofuranyl)-piperidine (see Example 32) is dissolved in 800 ml of toluene, and 80 g of chloroformic acid ethy ester added to the solution. The solution is refluxed for 15 hours with stirring, whereby during the first hour, to effect a more rapid removal of the liberated methyl chloride, a small amount of toluene is distilled off and thereafter provision made for complete refluxing of the toluene. The solution is subsequently cooled to 20°, filtered with suction, and the filter residue then washed with 100 ml of toluene. The combined filtrates are successively washed with 500 ml of water, 1 -liter of a 10% solution of methanesulphonic acid in water, 1 liter of water, 500 ml of 2 N sodium hydroxide solution, and 500 ml of water; they are then dried over sodium sulphate, filtered, and concentrated by evaporation. The resulting crude 4-(5,6-dimethyl-2-benzofuranyl)-1-piperidine-carboxylic acid ethyl ester melts at 96°–97° after recrystalisation from pentane.

36.5 g of 4-(5,6-dimethyl-2-benzofuranyl)-1-piperidinecarboxylic acid ethyl ester is dissolved in 150 ml of ethylene glycol. After the addition of 70 g of solid sodium hydroxide, the formed cloudy solution is heated, with vigorous stirring, for 15 hours at 160°. The reaction solution is thereupon cooled to 20°, and extracted twice with 500 ml of ethyl acetate each time. The organic phases are washed five times with 1 liter of water each time, dried over sodium sulphate, filtered, and concentrated by evaporation. The residue is dissolved in 300 ml of a 10% solution of methanesulphonic acid in water, and the acid solution extracted with ether. The aqueous solution is then adjusted by addition of 10% sodium hydroxide solution to have a pH value of 12, and extracted with 1 liter of chloroform. The chloroform solution is dried with sodium sulphate, filtered, and concentrated by evaporation to obtain crude 4-(5,6-dimethyl-2-benofuranyl)-piperidine. The free base melts at 77°–78° after recrystallisation from hexane. The hydrochloride is prepared with hydrogen chloride in ethyl acetate, and recrystallised from methanol-ethyl acetate, whereupon it is obtained in the form of the hydrate, which melts at 230°–233°.

Analogously there are obtained:

starting with 43 g of 1-methyl-4-(4,7-dimethyl-2-benzofuranyl)-piperidine [cp. Example 32] crude 4-(4,7-dimethyl-2-benzofuranyl)-1-piperidinecarboxylic acid ethyl ester, and from this: 4-(4,7-dimethyl-2-benzofuranyl)-piperidine and its hydrochloride, M.P. 266°.

starting with 43 g of 1-methyl-4-(5,7-dimethyl-2-benzofuranyl)-piperidine [cp. Example 32] crude 4-(5,7-dimethyl-2-benzofuranyl)-1-piperidinecarboxylic acid ethyl ester, and from this: 4-(5,7-dimethyl-2-benzofuranyl)-piperidine and its hydrochloride, M.P. 215°–218°, starting with 50 g of 1-methyl-4-[5-(trifluoromethyl)-2-benzofuranyl]-piperidine [cp. Example 32] crude 4-[5-(trifluoromethyl)-2-benzofuranyl]-1-piperidinecarboxylic acid ethyl ester, and from this: 4-[5-(trifluoromethyl)-2-benzofuranyl]-1-piperidine and its hydrochloride, and starting with 45 g of 1-methyl-4-[5,6-(trimethylene)-2-benzofuranyl]-piperidine [cp. Example 32] crude 4-[5,6-(trimethylene-2-benzofuranyl]-1-piperidinecarboxylic acid ethyl ester, and from this: 4-[5,6-(trimethylene)-2-benzofuranyl]-piperidine and its hydrochloride.

EXAMPLE 34

100 g of 4-(5,6-dimethyl-2-benzofuranyl)-piperidine [see Example 33] is dissolved in 50 ml of formic acid, and to this solution there is then added dropwise, with stirring, 6 ml of a 40% aqueous formaldehyde solution. The reaction mixture is heated for 5 hours at 95°–100°, and subsequently stirred for 15 hours at room temperature. The solution is thereupon rendered strongly acid by addition of 10 ml of conc. hydrochloride acid, and the solvent evaporated off under vacuum. The evaporation residue is dissolved in 100 ml of water, and the non-basic substances are extracted with toluene; the aqueous phase is adjusted by addition of 10% aqueous sodium hydroxide solution of pH 12, and extracted three times with 300 ml of chloroform each time. The organic phases are combined, dried over sodium sulphate, filtered, and concentrated by evaporation. The residue is chromatographed through 500 g of aluminium oxide [activity II, neutral]. The first fraction eluted with 500 ml of methylene chloride is, according to thin-layer analysis, not homogeneous and is not further processed. The second fraction eluted with 500 ml of methylene chloride is pure 1-methyl-4-(5,6-dimethyl-2-benzofuranyl)-piperidine. After recrystallisation from cyclohexane, the compound melts at 122°–124° and is identical to the compound of Example 32.

EXAMPLE 35

7.0 g of 4-(2-benzofuranyl)-1,3-dimethyl-4-piperidinol is refluxed in 100 ml of glacial acetic acid and 30 ml of hydrochloric acid for 10 hours. The solution is cooled, and extracted three times with 200 ml of chloroform each time. The organic phases are washed with 2 N sodium hydroxide solution, dried over sodium sulphate, filtered, and concentrated by evaporation. The crude 4-(2-benzofuranyl)-1,5-dimethyl-1,2,3,6-tetrahydropiperidine remaining behind melts at 242° to 244° after recrystallisation from ethyl acetate.

The starting material is prepared as follows:

50 ml of a bimolar solution of n-butyl lithium in hexane is added dropwise within 30 minutes, at a reaction temperature of −5°, to a solution of 11.8 g of benzofuran in 100 ml of diethyl ether. The solution is then stirred for a further hour at 0°. There is thereupon made within 15 minutes a dropwise addition of a solution of 1,3-dimethyl-4-piperidone in 50 ml of abs. diethyl ether. The reaction temperature is maintained at 0° by external cooling. The reaction solution is subsequently stirred for a further 15 hours at room temperature. It is then poured, with stirring, onto 200 g of ice, and the aqueous phase extracted three times with 500 ml of ethyl acetate each time. The combined organic extracts are dried over sodium sulphate, filtered, and concentrated by evaporation. The residue is dissolved in 500 ml of 2 N hydrochloric acid and the acid solution washed with ether. The aqueous solution is thereupon adjusted by addition of 10% sodium hydroxide solution to pH 12, and extracted with 1 liter of chloroform. The chloroform solution is dried with sodium sulphate, filtered off under suction, and concentrated by evaporation to obtain 4-(2-benzofuranyl)-1,3-dimethyl-4-piperidinol, which melts at 128°–130° after recrystallisation from hexane.

EXAMPLE 36

480 ml of a 1.35 N solution of n-butyl lithium in abs. diethyl ether is added dropwise within 30 minutes at −5° to a solution of 60 g of 1-methyl-4-(5-bromo-2-benzofuranyl)-piperidine [cp. Example 19] in 300 ml of diethyl ether. The reaction temperature during the dropwise addition is maintained at between −50° and 0° by external cooling. The solution is afterwards stirred for a further 90 minutes at 5° to 10°. There is then added dropwise within 30 minutes a solution of 85 ml of cyclohexanone in 100 ml of abs. diethyl ether, with the reaction temperature being kept at 0° to 5° by external cooling. The reaction solution is subsequently stirred for 15 hours at room temprature, and then poured, with stirring, onto 300 g of ice, and the aqueous phase extracted three times with 500 ml of ethyl acetate each time. The combined organic extracts are dried over sodium sulphate, filtered, and concentrated by evaporation. The residue is dissolved in 300 ml of 2 N hydrochloric acid, and the acid solution washed with ether. The aqueous solution is then adjusted by addition of 10% sodium hydroxide solution to pH 12, and extracted with 1000 ml of chloroform. The chloroform solution is dried with sodium sulphate, filtered off, and concentrated by evaporation to obtain crude 1-methyl-4-[5-(1-hydroxycyclohexyl)-2-benzofuranyl]-piperidine. The free base melts at 155° to 157° after recrystallisation from cyclohexane. The hydrochloride is prepared with hydrogen chloride in ethyl acetate, and recrystallised from acetone, whereupon it melts at 226°–229°.

EXAMPLE 37

20 g of 1-methyl-4-[5-(1-hydroxycyclohexyl)-2-benzofuranyl]-piperidine is refluxed in 60 ml of glacial acetic acid and 15 ml of hydrochloric acid for 48 hours. The reaction solution is cooled to room temperature, and concentrated in vacuo. The residue is suspended in 1000 ml of chloroform, and washed with 2 N sodium hydroxide solution. The organic phase is dried over sodium sulphate, filtered, and chromatographed through 700 g of aluminium oxide (activity II, neutral). The first fractions eluted with 3000 ml of chloroform yield, after concentration by evaporation, crude 1-methyl-4-[5-(1-cyclohexenyl)-2-berzofuranyl]-piperidine. After recrystallisation from hexane, the compounds melts at 81° to 85°. The hydrochloride prepared with a solution of hydrogen chloride in ethyl acetate melts at 227°–229° after recrystallisation from ethyl acetate.

EXAMPLE 38

2.0 g of 1-methyl-4-[5-(1-cyclohexenyl)-2-benzofuranyl]-piperidine is dissolved in 30 ml of methanol, and hydrogenated in the presence of 0.2 g of palladium-charcoal catalyst (5% Pd) at a temperature of 20°–25° and under normal pressure. Hydrogenation is terminated after 3 hours with attainment of 100% hydrogen absorption; the catalyst is filtered off, and the filtrate concentrated in vacuo. The resulting 1-methyl-4-(5-cyclohexyl-2-benzofuranyl)-piperidine melts at 89°–90° after recrystallisation from hexane. The hydrochloride prepared with a solution of hydrogen chloride in ethyl acetate melts at 238°–240° after recrystallisation from ethyl acetate.

EXAMPLE 39

A solution of 50 g of sodium borohydride in 100 ml of water is added dropwise, with stirring and external cooling, to a solution of 56.0 g of 1-methyl-3-(2-benzofuranyl)-piperidinium-iodide in 600 ml of methanol, the manner of addition being such that the reaction temperature does not exceed 35°. The solution is subsequently stirred for 15 hours at room temprature and again a solution of 50 g of sodium borohydride in 100 ml of water is added dropwise at a temperature not exceeding 35°. The methanol is thereupon evaporated off in vacuo; the aqueous phase remaining behind is extracted twice with 300 ml of chloroform each time, the chloroform solution dried over sodium sulphate, filtered, and concentrated by evaporation. The 1-methyl-3-(2-benzofuranyl)-1,2,3,6-tetrahydropyridine obtained is recrystallised from di-isopropylether, and then melts at 63°. The hydrochloride prepared therefrom with a solution of hydrogen chloride in ethyl acetate melts, after recrystallisation from ethyl acetate, at 244°–246°.

(a) 40 g of 3-(2-benzofuranyl)-pyridino [Chim. Ther. 6, 159–166 (1971)] is dissolved in 300 ml of methanol, and the solution stirred with 100 ml of methyl iodide for 15 hours at 40°–45°. The solution is then cooled to 0° to −5°, and the precipitated salt filtered off with suction. The filter residue is subsequently washed with 300 ml of isopropanol. After recrystallisation from isopropanol, the resulting 1-methyl-3-(2-benzofuranyl)-pyridinium-iodide melts at 222°.

EXAMPLE 40

20.2 g of 1-methyl-3-(2-benzofuranyl)-1,2,5,6-tetrahydropyridine [cp. Example 39] is dissolved in 300 ml of methanol, and the solution hydrognated in the presence of 6 g of palladium charcoal catalyst (5% Pd) at a temperature of between 40° and 50° and under normal pressure. After 44 hours 2.1 liters of hydrogen corresponding exactly to the theoretical amount has been absorbed. Hydrogenation is terminated, the catalyst filtered off, and the filtrate concentrated in vacuo. The residue is fractionally distilled in high vacuum. The fraction distilling at 108° to 110° and 0.09 Torr is 3-(2-benzofuranyl)-piperidine. The hydrochloride prepared from a solution of the base with a solution of hydrogen chloride in ethyl acetate melts at 193°–195°.

EXAMPLE 41

11.2 g of 1-methyl-3-(2-benzofuranyl)-piperidine (see Example 40) is dissolved in 100 ml of toluene, and 22.5 g of chloroformic acid ethyl ester added to the solution. The solution is refluxed for 15 hours with stirring, whereby during the first hour, to effect a more rapid removal of the liberated methyl chloride, a small amount of toluene is distilled off and thereafter provision made for complete refluxing of the toluene. The solution is subsequently cooled to 70°, filtered with suction, and the filter residue then washed with 500 ml of toluene. The combined filtrates are successively washed with 500 ml of water, 1 liter of a 10% solution of methanesulphonic acid in water, 1 liter of water, 500 ml of 2 N sodium hydroxide solution and 500 ml of water; they are then dried over sodium sulphate, filtered, and concentrated by evaporation. The resulting crude 3-(2-benzofuranyl)-1-piperidinecarboxylic acid ethyl ester is further processed without purification.

12.2 g of 3-(2-benzofuranyl)-1-piperidine-carboxylic acid ethyl ester is dissolved in 150 ml of ethylene glycol. After the addition of 50 g of solid sodium hydroxide, the formed cloudy solution is heated, with vigorous stirring, for 15 hours at 160°; the reaction solution is thereupon cooled to 20°, and extracted twice with 500 ml of toluene each time.

The organic phases are washed five times with 1 liter of water each time, dried over sodium sulphate, filtered, and concentrated by evaporation. The residue is dissolved in 300 ml of a 10% solution of methanesulphonic acid in water, and the acid solution extracted with ether. The aqueous solution is then adjusted by addition of 10% sodium hydroxide solution to have a pH value of 12, and extracted with 1 liter of chloroform. The chloroform solution is dried with sodium sulphate, filtered, and concentrated by evaporation. The residue is distilled in high vacuum (short way distillation), whereby 3-(2-benzofuranyl)-piperidine distills at 160°–166° and 0.2 Torr. The hydrochloride is prepared from this base with hydrogen chloride in ethyl acetate, and recrystallized from ethyl acetate, whereupon it melts at 216°–218°.

EXAMPLE 42

17.4 g of 2-(2-benzofuranyl)-pyridine is dissolved in 180 ml of methanol, and the solution hydrogenated in the presence of 1.8 g of palladium charcoal (5% at a temperature of between 40° and 50° and with an initial pressure of 3 bars (Paar apparatus). After 26 hours 5.06 liters of hydrogen has been absorbed. Hydrogenation is terminated, the catalyst filtered off, and the filtrate concentrated in vacuo. The residue is dissolved in 400 ml of 2 N hydrochloric acid and the acid solution is extracted with 1 liter of chloroform. The chloroform solution is dried with sodium sulphate, filtered and concentrated by evaporation. The residue is fractionally distilled in high vacuum. The fraction distilling at 112° to 116° and 0.15 Torr is 2-(2-benzofuranyl)-piperidine. The hydrochloride prepared from this with a solution of hydrogen chloride in ethyl acetate melts, after recrystallisation from acetone, at 222°–225°.

EXAMPLE 43

6.15 g of sodium borohydride dissolved in 50 ml of water is added dropwise in the course of 30 minutes, with stirring and ice-water cooling, to a solution of 18.2 g of 1-methyl-2-(2-benzofuranyl)-pyridinium-iodide in 150 ml of methanol. Stirring is maintained for 1 hour at room temperature, and the light-yellow solution then poured into 1000 ml of water. The precipitating oil is extracted with chloroform; the chloroform extracts are dried over anhydrous sodium sulphate, and the solvent distilled off in vacuo. The oily residue is taken up in a little methylene chloride, and chromatographed through 150 g of aluminum oxide (2% water). The methylene chloride eluates yield after concentration by evaporation 13.2 g of 1-methyl-2-(2-benzofuranyl)-1,4,5,6-tetrahydropyridine in the form of light-yellow oil. This is dissoled in 130 ml of ethyl acetate and, after the addition of 1 g of palladium-charcoal catalyst (10%), hydrogenated at room temperature. After absorption of 935 ml of hydrogen in the course of 19 hours, hydrogenation ceases. The catalyst is filtered off, the filtrate concentrated in vacuo, and the residue distilled in high vacuum to obtain 1-methyl-2-(2-benzofuranyl)-piperidine as colourless oil, B.P. 93°–97° (0.02 Torr). The hydrochloride is obtained as colourless crystals, M.P. 188°–189°, by dissolving the distilled base in the fivefold amount of acetone, and neutralising the solution with a 2 N solution of hydrogen chloride in ethyl acetate.

The starting material can be prepared in the following manner:

(a) 12.2 g of salicylaldehyde and 16.4 g of 2-(chloromethyl)-pyridine-hydrochloride are, after the addition of 55.2 g of potassium carbonate and 0.2 g of potassium iodide in 200 ml of isopropanol, refluxed for 12 hours with thorough stirring. The hot reaction mixture is filtered, and concentrated in vacuo. The residue is dissolved in 100 ml of chloroform, and the solution extracted with 2 N sodium hydroxide solution and then with water. The chloroform solution is subsequently dried over anhydrous sodium sulphate, and concentrated in vacuo. The oil remaining is dissolved in benzene, and filtered through 200 g. of aluminium oxide (2% water). The filtrates are concentrated by evaporation, and the residue distilled in high vacuum to obtain 2-(2-pyridylmethoxy)-benzaldehyde as colourless viscous oil, B.P. 135°–164°/0.04 Torr, which, after solidification, melts at 69°–71°. This substance is heated for 30 minutes at 300° in a nitrogen atomosphere; after cooling, it is dissolved in methylene chloride, and the solution filtered through aluminium oxide (2% water). From the filtrate there is obtained 2-(2-benzofuranyl)-pyridine in the form of yellowish crystals, M.P. 86°–87° (from isopropanol).

(b) 19.5 g of 2-(2-benzofuranyl)-pyridine is dissolved in 150 ml of methanol, and the solution heated, in an autoclave, with 42.9 g of methyl iodide for 17 hours at 120°. After cooling, the 1-methyl-2-(2-benzofuranyl)-pyridinium-iodide which has crystallised out is filtered off under suction, and subsequently thoroughly washed with isopropanol. The product is purified by recrystallisation from methanol/ether, whereupon deep-orange-coloured crystals, M.P. 179°–180°, are obtained.

EXAMPLE 44

A solution of 23.2 g of sodium borohydride in 60 ml of water is added dropwise, with stirring and external cooling, to a solution of 24.8 g (0.07 mole) of 1-methyl-4-(5-fluoro-2-benzofuranyl)-pyridinium-iodide in 200 ml of methanol, the manner of addition being such that the reaction temperature does not exceed 35°. The solution is subsequently stirred for 20 hours at room temperature. The methanol is thereupon evaporated off in vacuo; the aqueous phase remaining is extracted twice with 500 ml of chloroform each time; the chloroform solution is dried over sodium sulphate, filtered and then concentrated by evaporation. The residue is distilled in high vacuum (molecular distillation). The fraction passing over at 170° and 0.1 Torr is 1-methyl-4-(5-fluoro-2-benzofuranyl)-1,2,3,6-tetrahydropyridine, which melts at 117° to 119° after recrystallisation from hexane. The hydrochloride prepared therefrom with a solution of hydrogen chloride in ethyl acetate melts, after recrystallisation from methyl ethyl ketone, at 252°.

In an analogous manner there are obtained:

from 26.0 g of 1-methyl-4-(6-chloro-2-benzofuranyl)-pyridinium-iodide: 1-methyl-4-(6-chloro-2-benzofuranyl)-1,2,3,6-tetrahydropyridine, and from that its hydrochloride, m.p. 281°;

from 24.6 g of 1-methyl-4-(6-methyl-2-benzofuranyl)-pyridinium-iodide: 1-methyl-4-(6-methyl-2-benzofuranyl)-1,2,3,6-tetrahydropyridine, and from that its hydrochloride, m.p. 264°;

from 25.7 g of 1-methyl-4-(6-methoxy-2-benzofuranyl)pyridinium-iodide: 1-methyl-4-(6-methoxy-2-benzofuranyl)-1,2,3,6-tetrahydropyridine, and from that its hydrochloride, m.p. 279°;

from 28.4 g of 1-methyl-4-(5,7-dichloro-2-benzofuranyl)-pyridinium-iodide: 1-4-(5,7-dichloro-2-benzofuranyl)-1,2,3,6-tetrahydropyridine, and from that its hydrochloride, m.p. 286°;

from 27.0 g of 1-methyl-4-(5-chloro-6-methyl-2-benzofuranyl)-pyridinium-iodide: 1-methyl-4-(5-chloro-6-methyl-2-benzofuranyl)-1,2,3,6-tetrahydropyridine, and from that its hydrochloride, m.p. 262°-263°; and from 31.2 g of 1-methyl-4-(5-methoxy-7-bromo-2-benzofuranyl)-pyridinium-iodide: 1-methyl-4-(5-methoxy-7-bromo-2-benzofuranyl)-1,2,3,6-tetrahydropyridine, and from that its hydrochloride, m.p. 257°.

The starting materials can be produced in the following manner:

(a) 16.8 g (0.12 mole) of 5-fluorosalicylaldehyde, 27.8 g (0.17 mole) of 4-(chloromethyl)-pyridine-hydrochloride, 105 g of potassium carbonate and 3.0 g of potassium iodide are heated in 160 ml of dimethylformamide, with stirring, for 20 hours at 150° under nitrogen. The reaction mixture is thereupon cooled to 120°, and at this temperature filtered under suction. The filter residue is heated with 200 ml of dimethylformamide at 100° and subsequently washed with dimethylformamide. The combined filtrates are concentrated in vacuo; the volatile constituents are then removed by heating for 2 hours at 80° in high vacuum. The residue is dissolved in a small amount of methylene chloride, and chromatographed on 800 g of aluminium oxide (activity II, neutral). The first fraction, eluted with 2 liters of methylene chloride, is 4-(5-fluoro-2-benzofuranyl)-pyridine, which melts at 100°-102° after recrystallisation from isopropanol.

There are obtained in an analogous manner with the use of 18.9 g of 4-chlorosalicylaldehyde: 4-(6-chloro-2-benzofuranyl)-pyridine, the hydrochloride of which melts at 225°-230°;

with the use of 16.3 g of 4-methylsalicylaldehyde: 4-(6-methyl-2-benzofuranyl)-pyridine, m.p. 143°-144° (from cyclohexane);

with the use of 18.2 g of 4-methoxysalicylaldehyde: 4-(6-methoxy-2-benzofuranyl)-pyridine, the hydrochloride of which melts at 240°;

with the use of 22.9 g of 3,5-dichlorosalicyladehyde: 4-(5,7-dichloro-2-benzofuranyl)-pyridine, the hydrochloride of which melts at 255°;

with the use of 20.5 g of 4-methyl-5-chlorosalicylaldehyde: 4-(5-chloro-6-methyl-2-benzofuranyl)-pyridine (crude product);

with the use of 27.7 g of 3-bromo-5-methoxysalicylaldehyde: 4-(5-methoxy-7-bromo-2-benzofuranyl)-pyridine, of which the hydrochloride melts at 243°.

(b) 18.5 g (0.087 mole) of 4-(5-fluoro-2-benzofuranyl)-pyridine is dissolved in 170 ml of methanol, and the solution is stirred with 57 ml of methyl iodide for 15 hours at 40°-45°. The solution is thereupon cooled to −10°, and the precipitated salt is filtered off with suction. The filter residue is subsequently washed with 100 ml of cold isopropanol. The 1-methyl-4-(5-fluoro-2-benzofuranyl)-pyridinium-iodide thus obtained can be directly further processed.

The following are obtained in an analogous manner: from 20.0 g of 4-(6-chloro-2-benzofuranyl)-pyridine: 1-methyl-4-(6-chloro-2-benzofuranyl)-pyridinium-iodide;

from 18.2 g of 4-(6-methyl-2-benzofuranyl)-pyridine: 1-methyl-4-(6-methyl-2-benzofuranyl)-pyridinium-iodide;

from 19.6 g of 4-(6-methoxy-2-benzofuranyl)-pyridine: 1-methyl-4-(6-methoxy-2-benzofuranyl)-pyridinium-iodide;

from 23.0 g of 4-(5,7-dichloro-2-benzofuranyl)-pyridine: 1-methyl-4-(5,7-dichloro-2-benzofuranyl)-pyridinium-iodide;

from 21.3 g of 4-(5-chloro-6-methyl-2-benzofuranyl)-pyridine: 1-methyl-4-(5-chloro-6-methyl-2-benzofuranyl)-pyridinium-iodide; and from 26.5 g of 4-(5-methoxy-7-bromo-2-benzofuranyl)-pyridine: 1-methyl-4-(5-methoxy-7-bromo-2-benzofuranyl)-pyridinium-iodide.

EXAMPLE 45

13.9 g (0.06 mole) of 1-methyl-4-(5-fluoro-2-benzofuranyl)-1,2,3,6-tetrahydropyridine is dissolved in 250 ml of methanol, and the solution is hydrogenated in the presence of 0.7 g of palladium charcoal catalyst (5% Pd) at a temperature of between 15° and 20° under normal pressure. After 17 hours, there have been absorbed 1.376 liters of hydrogen, which corresponds exactly to the theroretical hydrogen consumption. Hydrogenation is interrupted, the catalyst is filtered off, and the filtrate is concentrated in vacuo. The residue is distilled in high vacuum (molecular distillation). The fraction passing over at 150° and 0.1 Torr is 1-methyl-4-(5-fluoro-2-benzofuranyl)-piperidine, which melts at 75°-76° after recrystallisation from pentane. The hydrochloride prepared from a solution of the base with a solution of hydrogen chloride in ethyl acetate melts, after recrystallisation from ethyl methyl ketone, at 228°.

In an analogous manner there are obtained:

from 14.9 g of 1-methyl-4-(6-chloro-2-benzofuranyl)-1,2,3,6-tetrahydropyridine: 1-methyl-4-(6-chloro-2-benzofuranyl)-piperidine, and from that its hydrochloride, m.p. 295°;

from 13.6 g of 1-methyl-4-(6-methyl-2-benzofuranyl)-1,2,3,6-tetrahydropyridine: 1-methyl-4-(6-methyl-2-benzofuranyl)-piperidine, and from that its hydrochloride, m.p. 222°;

from 14.6 g of 1-methyl-4-(6-methoxy-2-benzofuranyl)-1,2,3,6-tetrahydropyridine: 1-methyl-4-(6-methoxy-2-benzofuranyl)-piperidine, and from that its hydrochloride, m.p. 205°;

from 16.9 g of 1-methyl-4-(5,7-dichloro-2-benzofuranyl)-1,2,3,6-tetrahydropyridine: 1-methyl-4-(5,7-dichloro-2-benzofuranyl)-piperidine, and from that its hydrochloride, m.p. 258°-260°;

from 15.7 g of 1-methyl-4-(5-chloro-6-methyl-2-benzofuranyl)-1,2,3,6-tetrahydropyridine: 1-methyl-4-(5-chloro-6-methyl-2-benzofuranyl)-piperidine, and from that its hydrochloride, m.p. 224°; and from 16.9 g of 1-methyl-4-(5-methoxy-7-bromo-2-benzofuranyl)-1,2,3,6-tetrahydropyridine: 1-methyl-4-(5-methoxy-7-bromo-2-benzofuranyl)-piperidine, and from that its hydrochloride, m.p. 229°.

EXAMPLE 46

9.35 g (0.04 mole) of 1-methyl-4-(5-fluoro-2-benzofuranyl)-piperidine is dissolved in 170 ml of toluene. 20.7 g of chloroformic acid ethyl ester is slowly added dropwise, whilst a vigorous flow of nitrogen is maintained to effect a more rapid removal of the liberated methyl chloride. The solution is thereupon stirred for 20 hours at 60°; it is then cooled, filtered with suction and the filter residue is washed with 241 ml of toluene. The combined filtrates are washed successively with 250 ml of water, 250 ml of an oily solution of methanesulphonic acid in water, 251 ml of water, 251 ml of 2 N sodium hydroxide solution and 500 ml of water; they are then dried over sodium sulphate, filtered and concentrated by evaporation. The 4-(5-fluoro-2-benzofuranyl-1-piperidinecarboxylic acid ethyl ester remaining is an oil, which is pure according to thin-layer chromatographic analysis and can be further processed without additional purification.

5.9 g (about 0.02 mole) of 4-(5-fluoro-2-benzofuranyl)-1-piperidinecarboxylic acid ethyl ester is dissolved in 65 ml of ethylene glycol. After the addition of 19.4 g of 86% potassium hydroxide, the cloudy solution formed is heated, with vigorous stirring, for 18 hours at 160°. The reaction solution is thereupon cooled to 100°, diluted with 65 ml of toluene and then cooled to 20°. The organic phases are firstly extracted twice with one liter of water each time, then four times with 200 ml of a 10% solution of methane sulphonic acid in water. The methanesulphonic acid solution is thereupon brought to the pH-value of 12 by the addition of 30% sodium hydroxide solution, and is subsequently extracted with one liter of chloroform. The chloroform solution is dried with sodium sulphate, filtered and concentrated by evaporation to thus obtain crude 4-(5-fluoro-2-benzofuranyl)-piperidine. The base is distilled by molecular distillation in high vacuum. The fraction distilling at 190°–200° and 0.05 Torr is 4-(5-fluoro-2-benzofuranyl)-piperidine. The hydrochloride is prepared with hydrogen chloride in ethyl acetate and recrystallised from ethyl acetate, whereupon it melts at 235°–237°.

There are obtained analogously starting with 10.0 g of 1-methyl-4-(6-chloro-2-benzofuranyl)-piperidine: 4-(6-chloro-2-benzofuranyl)-piperidine, and from that its hydrochloride, m.p. 237°;

starting with 9.2 g of 1-methyl-4-(6-methyl-2-benzofuranyl)-piperidine: 4-(6-methyl-2-benzofuranyl)-piperidine, and from that its hydrochloride, m.p. 220°;

starting with 9.8 g of 1-methyl-4-(6-methoxy-2-benzofuranyl)-piperidine: 4-(6-methoxy-2-benzofuranyl)-piperidine, and from that its hydrochloride, m.p. 208°;

starting with 11.4 g of 1-methyl-4-(5,7-dichloro-2-benzofuranyl)-piperidine: 4-(5,7-dichloro-2-benzofuranyl)-piperidine, and from that its hydrochloride;

starting with 10.6 g of 1-methyl-4-(5-chloro-6-methyl-2-benzofuranyl)-piperidine: 4-(5-chloro-6-methyl-2-benzofuranyl)-piperidine: and from that its hydrochloride, m.p. 190°;

starting with 13.0 g of 1-methyl-4-(5-methoxy-7-bromo-2-benzofuranyl)-piperidine: 4-(5-methoxy-7-bromo-2-benzofuranyl)-piperidine, and from that its hydrochloride, m.p. 223°;

starting with 11.75 g of 1-methyl-4-(5-bromo-2-benzofuranyl)-piperidine: 4-(5-bromo-2-benzofuranyl)-piperidine, and from that its hydrochloride, m.p. 268°; and starting with 11.9 g of 1-methyl-4-(5-cyclohexyl-2-benzofuranyl)-piperidine: 4-(5-cyclohexyl-2-benzofuranyl)-piperidine, and from that its hydrochloride, m.p. 228°.

EXAMPLE 47

A solution of 10 g of sodium borohydride in 25 ml of water is added dropwise, with stirring and external cooling, to a solution of 9.8 g of 1-(2-propynyl)-4-(5,6-dimethyl-2-benzofuranyl)-pyridinium-bromide in 150 ml of methanol, the manner of addition being such that the reaction temperature does not exceed 30°. The solution is then stirred for 15 hours at room temperature. The methanol is thereupon evaporated off in vacuo; the aqueous phase remaining is extracted twice with 250 ml of chloroform each time, and the chloroform solution is dried over sodium sulphate, filtered and concentrated by evaporation. The residue is dissolved in 200 ml of 10% aqueous methane-sulphonic acid, and the acid solution is washed with ether. The pH-value of the acid aqueous phase is brought to 12 by the addition of 30% sodium hydroxide solution, and the aqueous phase is then extracted with 1000 ml of chloroform. The chloroform solution is dried with sodium sulphate, filtered and concentrated by evaporation. The residue is dissolved in a small amount of methylene chloride, and the solution is chromatographed on 50 g of aluminium oxide (activity II, neutral). The first fraction eluted with 1000 ml of methylene chloride is 1-(2-propynyl-(5,6-dimethyl-2-benzofuranyl)-1,2,3,6-tetrahydropyridine. The hydrochloride thereof is prepared with hydrogen chloride in ethyl acetate, and recrystallised from ethyl methyl ketone, whereupon it melts at 260°.

The 1-(2-propynyl)-4-(5,6-dimethyl-2-benzofuranyl)-pyridinium-bromide used as starting material can be produced in the following manner:

(a) 8.5 g of 4-(5,6-dimethyl-2-benzofuranyl)-pyridine is dissolved in 150 ml of methanol, and the solution is refluxed with 6.0 g of 3-bromopropyne for 4 hours at boiling temperature. The solution is thereupon cooled to 20°, stirred with active charcoal, and filtered through purified diatomaceous earth. The filtrate is concentrated in vacuo, and the evaporation residue is recrystallised from acetone. The resulting 1-(2-propynyl)-4-(5,6-dimethyl-2-benzofuranyl)-pyridinium-bromide melts at 240°–242°.

EXAMPLE 48

14.2 g of 4-(5-cyclohexyl-2-benzofuranyl)-piperidine and 6.0 g of 3-bromopropyne are dissolved in 300 ml of methanol, and, after the addition of 50 g of potassium carbonate, the reaction mixture is stirred for 30 hours at room temperature. It is then filtered with suction; the filter residue is washed with 500 ml of chloroform; and the combined filtrates are concentrated in vacuo. The residue is dissolved in a small amount of methylene chloride, and the solution is chromatographed on 300 g of aluminium oxide (activity II, neutral). The first fractions, eluted with a total amount of 1000 ml of methylene chloride, contain 1-(2-propynyl)-4-(5-cyclohexyl-2-benzofuranyl)-piperidine. The crude base is converted with a solution of hydrogen chloride in ethyl acetate into the hydrochloride. This is recrystallised from ethyl acetate and then melts at 248°.

EXAMPLE 49

A solution of 19.0 g of 1-(cyclopropylcarbonyl)-4-(5-cyclohexyl-2-benzofuranyl)-piperidine in 150 ml of tetrahydrofuran is added dropwise to a solution, boiling under reflux, of 13.5 g of lithium aluminium hydride in 200 ml of tetrahydrofuran. The reaction mixture is then refluxed for a further 15 hours; it is afterwards cooled, and the unreacted lithium aluminium hydride is decomposed at −10° by means of 15 ml of water, 15 ml of 10% sodium hydroxide solution and 45 ml of water. The reaction solution is thereupon filtered with suction, the filter residue is washed with 100 ml of chloroform, and the combined filtrates are concentrated in vacuo. The residue is dissolved in 500 ml of 2 N hydrochloric acid, and the acid solution is washed with ether. The aqueous solution is subsequently brought to pH 12 by the addition of 10% sodium hydroxide solution, and extracted with one liter of chloroform. The chloroform solution is dried with sodium sulphate, filtered with suction and concentrated by evaporation to obtain crude 1-(cyclopropylmethyl)-4-(5-cyclohexyl-2-benzofuranyl)-piperidine. This is converted with hydrogen chloride in ethyl acetate into the hydrochloride, and this is recrystallised from ethyl acetate, whereupon it melts at 220°.

The starting material can be produced in the following manner:

7.35 g of cyclopropanecarbonyl chloride and 50 g of potassium carbonate are added to a solution of 17.1 g of 4-(5-cyclohexyl-2-benzofuranyl)-piperidine in 350 ml of dioxane, and the reaction solution is subsequently stirred for 15 hours at room temperature. It is then filtered with suction; the filter residue is washed with 1000 ml of chloroform, and the combined filtrates are concentrated in vacuo. The residue is dissolved in 350 ml of ethyl acetate, and the solution is washed successively with 2 N hydrochloric acid, water, 2 N ammonium hydroxide and water; it is afterwards dried over sodium sulphate, filtered, and concentrated by evaporation. The oily evaporation residue is homogeneous 1-(cyclopropylcarbonyl)-4-(5-cyclohexyl-2-benzofuranyl)-piperidine, which can be used directly for reduction with lithium aluminium hydride.

What we claim is:

1. A compound of the formula I a

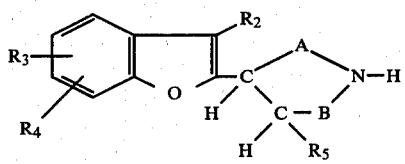

(Ia)

wherein $R_2$ represents hydrogen or lower alkyl, $R_3$ represents hydrogen, lower alkyl, lower alkoxy, halogen up to atomic number 35, benzyloxy, hydroxy, trifluoromethyl, 1-hydroxycycloalkyl, cycloalk-1-enyl or cycloalkyl, each of the three last-named groups having 5–8 carbon atoms, $R_4$ represents hydrogen, lower alkyl, lower alkoxy, halogen up to atomic number 35, benzyloxy or hydroxy, or $R_3$ and $R_4$ together represent trimethylene or tetramethylene or, corresponding to a fused-on benzene ring, the 1,3-butadienylene radical, $R_5$ represents hydrogen, or alkyl having at most 4 carbon atoms, and A and B represent methylene, ethylene, trimethylene or a direct bond, whereby A and B together always contain 3 chain members, or a pharmaceutically acceptable addition salt thereof with an inorganic or organic acid.

2. A compound according to claim 1 in which $R_2$ represents hydrogen or methyl, $R_3$ represents hydrogen, halogen up to atomic number 35, lower alkyl, lower alkoxy, trifluoromethyl, 1-hydroxycycloalkyl, cycloalk-1-enyl or cycloalkyl, each of the three last named groups having 5–8 carbon atoms, $R_4$ represents hydrogen, lower alkyl or halogen up to atomic number 35, or $R_3$ and $R_4$ together represent trimethylene in 5,6-position or, corresponding to a fused-on benzene ring, the 1,3-butadienylene radical in 4,5-position, $R_5$ represents hydrogen or methyl and A and B represent methylene, ethylene, trimethylene or the direct bond, account being taken of the sum of chain members fixed at 3, or a pharmaceutically acceptable acid addition salt thereof.

3. A compound according to claim 1 in which $R_2$ and $R_5$ represent hydrogen, $R_3$ represents hydrogen, halogen up to atomic number 35, methyl, methoxy or cyclohexyl, $R_4$ represents hydrogen, methyl, chlorine or bromine. A represents methylene and B ethylene or A represents ethylene and B methylene, or a pharmaceutically acceptable acid addition salt thereof.

4. A compound according to claim 1 in which $R_2$ and $R_5$ represent hydrogen, $R_3$ represents hydrogen, chlorine, bromine, methyl or methoxy, $R_4$ represents a hydrogen or methyl, A represents methylene and B ethylene, or A represents ethylene and B methylene, or a pharmaceutically acceptable acid addition salt thereof.

5. A compound according to claim 1 which is 4-(2-benzofuranyl)-piperidine, or a pharmaceutically acceptable acid addition salt thereof.

6. A compound according to claim 1 which is 4-(5,6-dimethyl-2-benzofuranyl)-piperidine, or a pharmaceutically acceptable acid addition salt thereof.

7. A compound according to claim 1 which is 3-(2-benzofuranyl)-piperidine, or a pharmaceutically acceptable acid addition salt thereof.

8. A compound according to claim 1 which is 4-(5-chloro-2-benzofuranyl)-piperidine, or a pharmaceutically acceptable acid addition salt thereof.

9. A compound according to claim 1 which is 4-(5-methoxy-2-benzofuranyl)-piperidine, or a pharmaceutically acceptable acid addition salt thereof.

10. A compound according to claim 1 which is 4-(5-methyl-2-benzofuranyl)-piperidine, or a pharmaceutically acceptable acid addition salt thereof.

11. A compound according to claim 1 which is 4-(5-fluoro-2-benzofuranyl)-piperidine, or a pharmaceutically acceptable acid addition salt thereof.

12. A compound according to claim 1 which is 4-(6-chloro-2-benzofuranyl)-piperidine, or a pharmaceutically acceptable acid addition salt thereof.

13. A compound according to claim 1 which is 4-(6-methyl-2-benzofuranyl)-piperidine, or a pharmaceutically acceptable acid addition salt thereof.

14. A compound according to claim 1 which is 4-(6-methoxy-2-benzofuranyl)-piperidine, or a pharmaceutically acceptable acid addition salt thereof.

15. A compound according to claim 1 which is 4-(5,7-dichloro-2-benzofuranyl)-piperidine, or a pharmaceutically acceptable acid addition salt thereof.

16. A compound according to claim 1 which is 4-(5-chloro-6-methyl-2-benzofuranyl)-piperidine, or a pharmaceutically acceptable acid addition salt thereof.

17. A compound according to claim 1 which is 4-(5-methoxy-7-bromo-2-benzofuranyl)-piperidine, or a pharmaceutically acceptable acid addition salt thereof.

18. A compound of the formula Ib

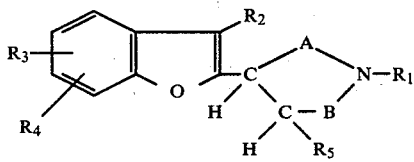

wherein
R$_1$ represents 2-propynyl or cyclopropylmethyl
R$_2$ represents hydrogen or lower alkyl,
R$_3$ represents hydrogen, lower alkyl, lower alkoxy, halogen up to atomic number 35, benzyloxy, hydroxy, trifluoromethyl, 1-hydroxycycloalkyl, cycloalk-1-enyl or cycloalkyl, each of the three last-named groups having 5–8 carbon atoms,
R$_4$ represents hydrogen, lower alkyl, lower alkoxy, halogen up to atomic number 35, benzyloxy or hydroxy, or
R$_3$ and R$_4$ together represent trimethylene or tetramethylene or, corresponding to a fused-on benzene ring, the 1,3-butadienylene radical,
R$_5$ represents hydrogen, or alkyl having at most 4 carbon atoms, and
A and B represent methylene, ethylene, trimethylene or a direct bond, whereby A and B together always contain 3 chain members, or a pharmaceutically acceptable addition salt thereof with an inorganic or organic acid.

19. A compound according to claim 18 in which R$_1$ has the meaning defined in claim 18, R$_2$ represents hydrogen or methyl, R$_3$ represents hydrogen, halogen up to atomic number 35, lower alkyl, lower alkoxy, trifluoromethyl, 1-hydroxycycloalkyl, cycloalk-1-enyl or cycloalkyl, each of the three last named groups having 5–8 carbon atoms, R$_4$ represents hydrogen, a lower alkyl group or halogen up to atomic number 35, or R$_3$ and R$_4$ together represent trimethylene in 5,6-position or, corresponding to a fused-on benzene ring, the 1,3-butadienylene radical in 4,5-position, R$_5$ represents hydrogen or methyl and A and B represent methylene, ethylene, trimethylene or the direct bond, account being taken of the sum of chain members fixed at 3, or a pharmaceutically acceptable acid addition salt thereof.

20. A compound according to claim 18 in which R$_1$ represents 2-propynyl or cyclopropylmethyl, R$_2$ and R$_5$ represents hydrogen, R$_3$ represents hydrogen, halogen up to atomic number 35, methyl, methoxy or cyclohexyl, R$_4$ represents hydrogen, methyl, chlorine or bromine, A represents methylene and B ethylene or A represents ethylene and B methylene, or a pharmaceutically acceptable acid addition salt thereof.

21. A compound according to claim 18 in which R$_1$ represents 2-propynyl or cyclopropylmethyl, R$_2$ and R$_5$ represent hydrogen, R$_3$ represents hydrogen, chlorine, bromine, methyl or methoxy, R$_4$ represents hydrogen or methyl, A represents ethylene and B methylene, or a pharmaceutically acceptable acid addition salt thereof.

22. A compound according to claim 18 which is 1-(2-propynyl)-4-(2-benzofuranyl)-piperidine, or a pharmaceutically acceptable acid addition salt thereof.

23. A compound according to claim 18 which is 1-(cyclopropylmethyl)-4-(2-benzofuranyl)-piperidine, or a pharmaceutically acceptable acid addition salt thereof.

24. A compound according to claim 18 which is 1-(2-propynyl)-4-(5,6-dimethyl-2-benzofuranyl)-piperidine, or a pharmaceutically acceptable acid addition salt thereof.

25. A compound according to claim 18 which is 1-(cyclopropylmethyl)-4-(5,6-dimethyl-2-benzofuranyl)-piperidine or a pharmaceutically acceptable acid addition salt thereof.

26. A compound according to claim 18 which is 1-(2-propynyl)-4-(5-cyclohexyl-2-benzofuranyl)-piperidine, or a pharmaceutically acceptable acid addition salt thereof.

27. A compound according to claim 18 which is 1-(cyclopropylmethyl)-4-(5-cyclohexyl-2-benzofuranyl)-piperidine, or a pharmaceutically acceptable acid addition salt thereof.

28. A compound which is 1-(3-oxo-butyl)-4-(2-benzofuranyl)-piperidine, or a pharmaceutically acceptable acid addition salt thereof.

29. A compound which is 1-(3-hydroxybutyl)-4-(2-benzofuranyl)-piperidine, or a pharmaceutically acceptable acid addition salt thereof.

30. A therapeutic composition for the treatment of mental depression in warm-blooded animals comprising a therapeutically effective amount of a compound according to claim 18 having the formula

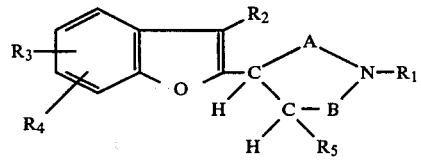

wherein
R$_1$ represents 2-propynyl or cyclopropylmethyl
R$_2$ represents hydrogen or lower alkyl,
R$_3$ represents hydrogen, lower alkyl, lower alkoxy, halogen up to atomic number 35, benzyloxy, hydroxy, trifluoromethyl, 1-hydroxycycloalkyl, cycloalk-1-enyl or cycloalkyl, each of the three last-named groups having 5–8 carbon atoms,
R$_4$ represents hydrogen, lower alkyl, lower alkoxy, halogen up to atomic number 35, benzyloxy or hydroxy, or
R$_3$ and R$_4$ together represent trimethylene or tetramethylene or, corresponding to a fused-on benzene ring, the 1,3-butadienylene radical,
R$_5$ represents hydrogen, or alkyl having at most 4 carbon atoms, and
A and B represent methylene, ethylene, trimethylene or a direct bond, whereby A and B together always contain 3 chain members, or a pharmaceutically acceptable addition salt thereof with an inorganic or organic acid, together with a pharmaceutical carrier.

31. A therapeutic composition according to claim 30, wherein a compound of the formula Ib given in claim 30, in which R$_1$ has the meaning defined in claim 30, R$_2$ represents hydrogen or methyl, R$_3$ represents hydrogen, halogen up to atomic number 35, lower alkyl, lower alkoxy, trifluoromethyl, 1-hydroxycycloalkyl, cycloalk-1-enyl or cycloalkyl, each of the three last named groups having 5–8 carbon atoms, R$_4$ represents hydrogen, a lower alkyl group or halogen up to atomic number 35, or R$_3$ and R$_4$ together represent trimethylene in 5,6-position or, corresponding to a fused-on benzene ring, the 1,3-butadienylene radical in 4,5-position, R$_5$ represents hydrogen or methyl and A and B represent methylene, ethylene, trimethylene or the direct bond, account being taken of the sum of chain members fixed at 3, or a pharmaceutically acceptable acid addition salt thereof is present.

32. A therapeutic composition according to claim 30, wherein a compound of the formula Ib given in claim 30, in which $R_1$ represents 2-propynyl or cyclopropylmethyl, $R_2$ and $R_5$ represents hydrogen, $R_3$ represents hydrogen, halogen up to atomic number 35, methyl, methoxy or cyclohexyl, $R_4$ represents hydrogen, methyl, chlorine or bromine, A represents methylene and B ethylene or A represents ethylene and B methylene, or a pharmaceutically acceptable acid addition salt thereof is present.

33. A therapeutic composition according to claim 30, wherein a compound of the formula Ib given in claim 30, in which $R_1$ represents 2-propynyl or cyclopropylmethyl, $R_2$ and $R_5$ represent hydrogen, $R_3$ represents hydrogen, chlorine, bromine, methyl or methoxy, $R_4$ represents hydrogen or methyl, A represents ethylene and B methylene, or a pharmaceutically acceptable acid addition salt thereof is present.

* * * * *